United States Patent
Mun et al.

(10) Patent No.: US 10,518,205 B2
(45) Date of Patent: Dec. 31, 2019

(54) AIR CLEANER

(71) Applicant: LG ELECTRONICS INC., Seoul (KR)

(72) Inventors: Yeongcheol Mun, Seoul (KR); Hyunpil Ha, Seoul (KR); Soonki Jung, Seoul (KR); Jaekyun Park, Seoul (KR); Soohyun Bae, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/363,438

(22) Filed: Nov. 29, 2016

(65) Prior Publication Data
US 2017/0246579 A1 Aug. 31, 2017

(30) Foreign Application Priority Data

Feb. 26, 2016 (KR) .................. 10-2016-0023663
Jun. 15, 2016 (KR) .................. 10-2016-0074369
Oct. 25, 2016 (KR) .................. 10-2016-0139376

(51) Int. Cl.
*B01D 19/00* (2006.01)
*B01D 46/00* (2006.01)
(Continued)

(52) U.S. Cl.
CPC ............ *B01D 46/0047* (2013.01); *A61L 9/22* (2013.01); *B01D 46/002* (2013.01);
(Continued)

(58) Field of Classification Search
CPC ............... B01D 46/00; B01D 46/0005; B01D 46/0008; B01D 46/002; B01D 46/0047;
(Continued)

(56) References Cited

U.S. PATENT DOCUMENTS 4,210,429 A   7/1980   Golstein
4,365,980 A  12/1982   Culbert et al.
(Continued)

FOREIGN PATENT DOCUMENTS

CN   1487246   4/2004
CN   1510348   7/2004
(Continued)

OTHER PUBLICATIONS

International Search Report dated Mar. 20, 2017 issued in Application No. PCT/KR2016/013906.
(Continued)

*Primary Examiner* — T. Bennett McKenzie
(74) *Attorney, Agent, or Firm* — Ked & Associates LLP

(57) ABSTRACT

An air cleaner is provided that may include a case including a first suction inlet, the case having a cylindrical or cone shape; a fan housing provided inside of the case, the fan housing accommodating a fan therein; a filter provided at a suction side of the fan, the filter filtering foreign materials in air which is suctioned through the first suction inlet; and a housing suction flow path formed between an outer surface of the fan housing and an inner surface of the case, the housing suction flow path allowing air which is suctioned through the first suction inlet to flow toward and through the filter. The housing suction flow path may include a first flow path inlet having a predetermined first width, and a second flow path inlet through which air having passed through the first flow path inlet flows, the second flow path inlet having a second width greater than the first width.

21 Claims, 16 Drawing Sheets

(51) Int. Cl.
| | | |
|---|---|---|
| *F24F 13/20* | (2006.01) | |
| *F24F 13/28* | (2006.01) | |
| *F24F 3/16* | (2006.01) | |
| *B01D 46/24* | (2006.01) | |
| *B01D 46/44* | (2006.01) | |
| *A61L 9/22* | (2006.01) | |

(52) U.S. Cl.
CPC ..... *B01D 46/0005* (2013.01); *B01D 46/0008* (2013.01); *B01D 46/24* (2013.01); *B01D 46/2403* (2013.01); *B01D 46/442* (2013.01); *F24F 3/1603* (2013.01); *F24F 13/20* (2013.01); *F24F 13/28* (2013.01); *A61L 2209/111* (2013.01); *A61L 2209/14* (2013.01); *B01D 2273/30* (2013.01); *F24F 2013/205* (2013.01); *F24F 2013/207* (2013.01); *F24F 2221/12* (2013.01)

(58) Field of Classification Search
CPC .. B01D 46/24; B01D 46/2403; B01D 46/442; B01D 2273/20; B01D 2273/30; A61L 9/22; A61L 2209/111; A61L 2209/24; A61L 2209/11; A61L 2209/12; A61L 2209/14; F24F 3/1603; F24F 13/20; F24F 13/28; F24F 2013/205; F24F 2013/207; F24F 2221/12; F24F 3/16; F24F 7/007; F24F 13/10; F24F 13/12; F24F 13/14; F24F 2110/64; F24F 11/30; F24F 11/52; F24F 11/89; F24F 2001/0096; F04D 29/403; F04D 29/703
USPC ............ 55/467, 318–337, 385.1–385.8
See application file for complete search history.

(56) References Cited

U.S. PATENT DOCUMENTS

| | | | |
|---|---|---|---|
| 4,905,340 | A | 3/1990 | Gutschmit |
| 5,117,652 | A | 6/1992 | Takeuchi et al. |
| 5,264,015 | A | 11/1993 | Matsui |
| 5,334,248 | A | 8/1994 | Kwak |
| 5,641,343 | A | 6/1997 | Frey |
| 5,753,000 | A | 5/1998 | Chiu et al. |
| 5,837,020 | A * | 11/1998 | Cartellone ............. B01D 46/24 55/459.3 |
| 6,053,968 | A * | 4/2000 | Miller ....................... A61L 9/20 96/16 |
| 6,264,712 | B1 | 7/2001 | Decker |
| 6,280,493 | B1 | 8/2001 | Eubank |
| 6,494,940 | B1 | 12/2002 | Hak |
| 6,680,028 | B1 | 1/2004 | Harris |
| 6,955,708 | B1 | 10/2005 | Julos et al. |
| 8,212,146 | B1 | 7/2012 | Moore |
| 9,821,259 | B2 | 11/2017 | Bae et al. |
| 9,943,794 | B2 | 4/2018 | Jung |
| 9,950,289 | B2 | 4/2018 | Jung |
| 2002/0157415 | A1 | 10/2002 | Liu |
| 2004/0144249 | A1* | 7/2004 | Kang ................... F24F 3/1603 95/1 |
| 2005/0066634 | A1 | 3/2005 | Genn et al. |
| 2006/0107834 | A1 | 5/2006 | Vandenbelt et al. |
| 2006/0201119 | A1 | 9/2006 | Song |
| 2006/0277875 | A1 | 12/2006 | Schuld |
| 2007/0137489 | A1 | 6/2007 | Luo |
| 2007/0221061 | A1 | 9/2007 | Steiner et al. |
| 2008/0286163 | A1 | 11/2008 | Garfield |
| 2010/0225012 | A1 | 9/2010 | Fitton et al. |
| 2010/0225015 | A1 | 9/2010 | Techlin et al. |
| 2011/0033346 | A1 | 2/2011 | Bohlen |
| 2011/0308210 | A1 | 12/2011 | Crabtree et al. |
| 2013/0055692 | A1 | 3/2013 | Cecchi et al. |
| 2013/0090052 | A1 | 4/2013 | Akhtar |
| 2014/0020561 | A1* | 1/2014 | Aery ................. B01D 46/0021 96/224 |
| 2014/0102664 | A1 | 4/2014 | Kim et al. |
| 2014/0216251 | A1 | 8/2014 | Jun et al. |
| 2014/0216259 | A1 | 8/2014 | Iwaki |
| 2015/0273376 | A1 | 10/2015 | Sohn et al. |
| 2015/0306533 | A1 | 10/2015 | Matlin et al. |
| 2015/0345816 | A1 | 12/2015 | Donovan |
| 2016/0032942 | A1 | 2/2016 | Jung et al. |
| 2016/0184753 | A1 | 6/2016 | Chu et al. |

FOREIGN PATENT DOCUMENTS

| | | |
|---|---|---|
| CN | 1598413 | 3/2005 |
| CN | 1619229 | 5/2005 |
| CN | 1752617 | 3/2006 |
| CN | 2769724 | 4/2006 |
| CN | 1784258 | 6/2006 |
| CN | 101021345 | 8/2007 |
| CN | 101105307 | 1/2008 |
| CN | 201106913 | 8/2008 |
| CN | 201482362 | 5/2010 |
| CN | 102563752 | 7/2012 |
| CN | 102748817 | 10/2012 |
| CN | 202568987 | 12/2012 |
| CN | 103574770 | 2/2014 |
| CN | 103673076 | 3/2014 |
| CN | 103712318 | 4/2014 |
| CN | 103727632 | 4/2014 |
| CN | 203518040 | 4/2014 |
| CN | 103930730 | 7/2014 |
| CN | 103982994 | 8/2014 |
| CN | 203893332 | 10/2014 |
| CN | 203964288 | 11/2014 |
| CN | 102661295 | 12/2014 |
| CN | 204084651 | 1/2015 |
| CN | 104329785 | 2/2015 |
| CN | 204141826 | 2/2015 |
| CN | 104406235 | 3/2015 |
| CN | 104456772 | 3/2015 |
| CN | 104603545 | 5/2015 |
| CN | 204329221 | 5/2015 |
| CN | 204447560 | 7/2015 |
| CN | 104937359 | 9/2015 |
| CN | 104971567 | 10/2015 |
| CN | 104990155 | 10/2015 |
| CN | 105091106 | 11/2015 |
| CN | 105185242 | 12/2015 |
| CN | 105221452 | 1/2016 |
| CN | 204933080 | 1/2016 |
| CN | 204963008 | 1/2016 |
| CN | 105299862 | 2/2016 |
| CN | 105299863 | 2/2016 |
| CN | 105333499 | 2/2016 |
| CN | 105333528 | 2/2016 |
| CN | 206300285 | 7/2017 |
| CN | 206300287 | 7/2017 |
| CN | 206300288 | 7/2017 |
| CN | 206338921 | 7/2017 |
| DE | 9312051 | 10/1993 |
| EP | 1 950 500 | 7/2008 |
| EP | 2 072 920 | 6/2009 |
| EP | 2 476 968 | 7/2012 |
| EP | 2 837 897 | 2/2015 |
| EP | 2 853 835 | 4/2015 |
| GB | 995962 | 6/1965 |
| GB | 996962 | 6/1965 |
| GB | 2 345 005 | 6/2000 |
| GB | 2516058 | 1/2015 |
| JP | 04-008973 | 3/1992 |
| JP | H 04-103549 | 9/1992 |
| JP | H 06-50180 | 6/1994 |
| JP | 7-208779 | 8/1995 |
| JP | 2000-354724 | 12/2000 |
| JP | 2006-022977 | 1/2006 |
| JP | 2007-105578 | 4/2007 |
| JP | 4526372 | 8/2010 |
| JP | 2012-120720 | 6/2012 |
| JP | 2013-217580 | 10/2013 |

(56) References Cited

FOREIGN PATENT DOCUMENTS

| | | |
|---|---|---|
| JP | 2014-507277 | 3/2014 |
| JP | 2014-119224 | 6/2014 |
| JP | 2015-080737 | 4/2015 |
| JP | 2015-108497 | 6/2015 |
| JP | 5740503 | 6/2015 |
| JP | 2015-120138 | 7/2015 |
| JP | 5800652 | 10/2015 |
| JP | 2016-034602 | 3/2016 |
| KR | 20-1993-0002444 | 5/1993 |
| KR | 10-0139487 | 6/1998 |
| KR | 20-0173274 | 3/2000 |
| KR | 20-0289687 | 9/2002 |
| KR | 20-0342073 | 2/2004 |
| KR | 10-2004-0056151 | 6/2004 |
| KR | 10-2004-0108462 | 12/2004 |
| KR | 10-0508312 | 8/2005 |
| KR | 10-2005-0110233 | 11/2005 |
| KR | 10-2005-0115343 | 12/2005 |
| KR | 10-2006-0023457 | 3/2006 |
| KR | 10-2006-0026319 | 3/2006 |
| KR | 10-0674271 | 1/2007 |
| KR | 20-2008-0001777 | 6/2008 |
| KR | 10-2009-0058446 | 6/2009 |
| KR | 10-2009-0087652 | 8/2009 |
| KR | 10-2010-0056797 | 5/2010 |
| KR | 10-2010-0062121 | 6/2010 |
| KR | 10-2010-0070069 | 6/2010 |
| KR | 10-2010-0102507 | 9/2010 |
| KR | 10-2011-0029870 | 3/2011 |
| KR | 10-2012-0060279 | 6/2012 |
| KR | 10-2012-0071992 | 7/2012 |
| KR | 10-1168738 | 7/2012 |
| KR | 10-1203570 | 11/2012 |
| KR | 10-2012-0136137 | 12/2012 |
| KR | 10-2013-0036447 | 4/2013 |
| KR | 10-1278334 | 6/2013 |
| KR | 10-1342606 | 12/2013 |
| KR | 10-2014-0039703 | 4/2014 |
| KR | 10-1385290 | 4/2014 |
| KR | 10-2014-0092953 | 7/2014 |
| KR | 10-2014-0094414 | 7/2014 |
| KR | 10-2014-0096971 | 8/2014 |
| KR | 10-2015-0005594 | 1/2015 |
| KR | 10-1500501 | 3/2015 |
| KR | 10-1506653 | 3/2015 |
| KR | 10-1512664 | 4/2015 |
| KR | 10-1516365 | 5/2015 |
| KR | 10-2016-0012796 | 2/2016 |
| KR | 10-2016-0015084 | 2/2016 |
| KR | 10-2016-0017587 | 2/2016 |
| KR | 10-2016-0028292 | 3/2016 |
| KR | 10-1599634 | 3/2016 |
| KR | 10-2016-0048499 | 5/2016 |
| KR | 10-2016-0053649 | 5/2016 |
| KR | 10-2016-0104837 | 9/2016 |
| WO | WO 2010/109944 | 9/2010 |
| WO | WO 2013/121672 | 8/2013 |
| WO | WO 2015/171571 | 11/2015 |

OTHER PUBLICATIONS

Korean Office Action dated Apr. 12, 2018.
Korean Notice of Allowance dated Apr. 17, 2018.
Korean Notice of Allowance dated Jun. 11, 2018.
International Search Report dated Mar. 30, 2017 issued in Application No. PCT/KR2016/013912.
International Search Report dated Mar. 30, 2017 issued in Application No. PCT/KR2016/013908.
Korean Office Action dated Apr. 20, 2017 issued in Application No. 10-2016-0132790.
European Search Report dated Jun. 21, 2017 issued in Application No. 16201095.3.
European Search Report dated Jul. 14, 2017 issued in Application No. 14201092.0.
Korean Office Action dated Aug. 31, 2017 issued in Application No. 10-2016-0073063.
Korean Office Action dated Oct. 31, 2017.
U.S. Appl. No. 15/363,438, filed Nov. 29, 2016, Duane Smith.
U.S. Office Action issued in U.S. Appl. No. 15/364,369 dated Jul. 14, 2017.
United States Office Action dated Jan. 20, 2017 issued in U.S. Appl. No. 15/363,156.
United States Office Action dated Jan. 20, 2017 issued in U.S. Appl. No. 15/364,369.
United States Office Action dated Jan. 23, 2017 issued in U.S. Appl. No. 15/363,204.
United States Office Action dated Jan. 23, 2017 issued in U.S. Appl. No. 15/364,410.
United States Office Action dated Jan. 23, 2017 issued in U.S. Appl. No. 15/364,467.
Korean Office Action dated Jan. 26, 2017 issued in Application No. 10-2016-0073055.
Korean Office Action dated Jan. 26, 2017 issued in Application No. 10-2016-0073083.
Korean Office Action dated Jan. 26, 2017 issued in Application No. 10-2016-0077888.
International Search Report dated Mar. 21, 2017 issued in Application No. PCT/KR2016/013907.
United States Office Action dated Feb. 10, 2017 issued in co-pending U.S. Appl. No. 15/363,111.
U.S. Office Action issued in U.S. Appl. No. 15/363,643 dated Oct. 24, 2018.
U.S. Office Action issued in U.S. Appl. No. 15/441,957 dated Oct. 25, 2018.
United States Office Action dated Dec. 3, 2018 issued in co-pending related U.S. Appl. No. 15/363,587.
United States Office Action dated Feb. 6, 2019 issued in co-pending related U.S. Appl. No. 15/660,105.
United States Office Action dated Feb. 6, 2019 issued in co-pending related U.S. Appl. No. 15/660,122.
United States Office Action dated Feb. 21, 2019 issued in co-pending related U.S. Appl. No. 15/659,878.
U.S. Appl. No. 15/441,957, filed Feb. 24, 2017.
U.S. Appl. No. 15/660,105, filed Jul. 26, 2017.
Chinese Office Action dated Jan. 11, 2019 issued in Application No. 201611089233.9 (with English Translation).
U.S. Appl. No. 15/363,111, filed Nov. 29, 2016, Robert Arthur Clemente.
U.S. Appl. No. 15/363,156, filed Nov. 29, 2016, Robert Arthur Clemente.
U.S. Appl. No. 15/659,869, filed Jul. 26, 2017, Robert Arthur Clemente.
U.S. Appl. No. 15/659,878, filed Jul. 26, 2017, Robert Arthur Clemente.
U.S. Appl. No. 15/363,204, filed Nov. 29, 2016, Robert Arthur Clemente.
U.S. Appl. No. 15/364,467, filed Nov. 30, 2016, Robert Arthur Clemente.
U.S. Appl. No. 15/660,105, filed Jul. 26, 2017, Robert Arthur Clemente.
U.S. Appl. No. 15/660,122, filed Jul. 26, 2017, Robert Arthur Clemente.
U.S. Appl. No. 15/363,587, filed Nov. 29, 2016, Duane Smith.
U.S. Appl. No. 15/659,989, filed Jul. 26, 2017, Duane Smith.
U.S. Appl. No. 15/660,076, filed Jul. 26, 2017, Duane Smith.
U.S. Appl. No. 15/660,207, filed Jul. 26, 2017, Duane Smith.
U.S. Appl. No. 15/660,287, filed Jul. 26, 2017, Duane Smith.
U.S. Appl. No. 15/660,362, filed Jul. 26, 2017, Duane Smith.
U.S. Appl. No. 15/660,462, filed Jul. 26, 2017, Duane Smith.
U.S. Appl. No. 15/363,643, filed Nov. 29, 2016, Duane Smith.
U.S. Appl. No. 15/364,369, filed Nov. 30, 2016, Robert Arthur Clemente.
U.S. Appl. No. 15/364,410, filed Nov. 30, 2016, Robert Arthur Clemente.
U.S. Appl. No. 15/441,957, filed Feb. 24, 2017, Duane Smith.
European Search Report dated Jan. 17, 2018.
European Search Report dated Jan. 18, 2018.

(56) References Cited

OTHER PUBLICATIONS

Chinese Office Action dated Feb. 28, 2019 issued in Application No. 201611087595.4 (with English Translation).
Chinese Office Action dated Feb. 28, 2019 issued in Application No. 201611089358.1 (with English Translation).
U.S. Appl. No. 15/926,129, filed Mar. 20, 2018, Robert Arthur Clemente.
U.S. Appl. No. 15/363,587, filed Nov. 29, 2016, Thomas B. McKenzie.
U.S. Appl. No. 15/363,643, filed Nov. 29, 2016, Thomas B. McKenzie.
U.S. Appl. No. 16/409,017, filed May 10, 2019, Minh Chau Thi Pham.
Chinese Office Action dated Mar. 5, 2019 issued in Application No. 201611089126.6 (with English Translation).
Chinese Office Action dated Mar. 27, 2019 issued in Application No. 201611089196.1 (with English Translation).
Korean Office Action dated May 2, 2019 issued in Application No. 10-2019-0025204.
United States Office Action dated Mar. 5, 2019 issued in co-pending related U.S. Appl. No. 15/363,587.
European Search Report dated Jun. 21, 2017 issued in Application No. 16201093.8.
Korean Office Action dated Jun. 21, 2017 issued in Application No. 10-2017-0056789.
Korean Office Action dated Jun. 21, 2017 issued in Application No. 10-2017-0056790.
Korean Office Action dated Jun. 21, 2017 issued in Application No. 10-2017-0056791.
European Search Report dated Jun. 23, 2017 issued in Application No. 16201089.6.
European Search Report dated Jun. 23, 2017 issued in Application No. 16201088.8.
Korean Office Action dated Jun. 30, 2017 issued in Application No. 10-2017-0056864.
European Search Report dated Jul. 14, 2017 issued in Application No. 16201094.6.
European Search Report dated Jul. 20, 2017 issued in Application No. 16201091.2.
Korean Notice of Allowance dated Aug. 15, 2017 issued in Application No. 10-2016-0074369.
Korean Office Action dated Aug. 22, 2017 issued in Application No. 10-2016-0073055.
U.S. Office Action issued in U.S. Appl. No. 15/660,462, dated Jul. 19, 2019.
U.S. Office Action issued in U.S. Appl. No. 15/660,207, dated Jul. 22, 2019.
European Search Report dated Apr. 25, 2017 issued in Application No. 16201086.2-1602.
European Search Report dated Apr. 25, 2017 issued in Application No. 17157045.0-1602.
Korean Office Action dated Jun. 21, 2017 (10-2017-0056865).
Korean Office Action dated Jun. 21, 2017 (10-2017-0056885).
Korean Office Action dated Jun. 21, 2017 (10-2017-0056886).
Chinese Office Action dated Feb. 22, 2019 with English Translation.
U.S. Office Action issued in U.S. Appl. No. 15/660,076 dated May 8, 2019.
European Search Report dated Jul. 20, 2017 issued in Application No. 16201090.4.
Korean Office Action dated Aug. 31, 2017 issued in Application No. 10-2016-0073090.
U.S. Appl. No. 15/926,129, filed Mar. 20, 2018.
U.S. Appl. No. 15/659,869, filed Jul. 26, 2017.
U.S. Appl. No. 15/659,878, filed Jul. 26, 2017.
U.S. Appl. No. 15/660,122, filed Jul. 26, 2017.
U.S. Appl. No. 16/527,140, filed Jul. 31, 2019.
U.S. Appl. No. 15/363,587, filed Nov. 29, 2016.
U.S. Appl. No. 15/659,989, filed Jul. 26, 2017.
U.S. Appl. No. 15/660,076, filed Jul. 26, 2017.
U.S. Appl. No. 15/660,207, filed Jul. 26, 2017.
U.S. Appl. No. 15/660,287, filed Jul. 26, 2017.
U.S. Appl. No. 15/660,362, filed Jul. 26, 2017.
U.S. Appl. No. 15/660,462, filed Jul. 26, 2017.
U.S. Appl. No. 15/363,643, filed Nov. 29, 2016.
U.S. Appl. No. 16/548,045, filed Aug. 22, 2019.
U.S. Appl. No. 16/409,017, filed May 10, 2019.
Chinese Office Action dated Jun. 10, 2019 issued in Application No. 201710660027.7.
Chinese Office Action dated Jul. 29, 2019 issued in Application No. 201710659929.9.
Chinese Office Action dated May 27, 2019 issued in Application No. 201710637948.1 with English Translation.
Chinese Office Action dated Jun. 4, 2019 issued in Application No. 201710638173.X with English Translation.
Chinese Office Action dated Jun. 24, 2019 issued in Application No, 201710637920.8 with English Translation.
Chinese Office Action dated Jun. 26, 2019 issued in Application No. 201710790121.4 with English Translation.
Chinese Office Action dated Jun. 27, 2019 issued in Application No. 201710637967.4 with English Translation.
Chinese Office Action dated Jul. 16, 2019 issued in Application No. 201710638026.2. With English Translation.
Korean Notice of Allowance dated Jul. 1, 2019 issued in Application No. 10-2019-0063475.
U.S. Office Action issued in U.S. Appl. No. 15/660,287 dated Aug. 16, 2019.
United States Office Action dated Aug. 22, 2019 issued in co-pending related U.S. Appl. No. 15/926,129.
Korean Office Action dated Jul. 22, 2019 issued in KR Application No. 10-2019-0060135.
Japanese Office Action dated Aug. 20, 2019.
Chinese Office Action dated Oct. 25, 2019.

* cited by examiner

AIR CLEANER

CROSS-REFERENCE TO RELATED APPLICATION(S)

The present application claims priority under 35 U.S.C. 119 and 35 U.S.C. 365 to Korean Patent Application No. 10-2016-0074369 filed in Korea on Jun. 15, 2016, No. 10-2016-0023663 filed in Korea on Feb. 26, 2016, and No. 10-2016-0139376 filed in Korea on Oct. 25, 2016, which are hereby incorporated by reference in their entirety.

BACKGROUND

1. Field

An air cleaner is disclosed herein.

2. Background

An air cleaner is a device that suctions in and purifies contaminated air and then discharges purified air. For example, the air cleaner may include a blower that introduces outside air into the air cleaner and a filter capable of filtering dust and bacteria, for example.

Generally, the air cleaner is configured to purify an indoor space, such as a home or an office. According to the air cleaner in the related art, there is a problem that a capacity thereof is limited, and thus, purification of air in an entire indoor space is limited. Accordingly, air around the air cleaner is purified whereas air in a space away from the air cleaner is not purified.

In order to solve this problem, there are efforts to improve a performance of a fan provided in the air cleaner. However, noise generated by the fan gradually increases as a blowing amount of the fan increases. Accordingly, there is a problem is that reliability of the product is decreased. Finally, there is inconvenience that the air cleaner has to be moved by a user in order to purify air in the desired space.

A related art air cleaner is disclosed in Korean Publication No. KR10-2012-0071992 published on Jul. 3, 2012 and entitled AIR CLEANER, which is hereby incorporated by reference. According to this disclosure, air cleaning components, such as the fan and a filter are installed, in an inside of a case having a substantially rectangular parallelepiped shape of a main body of the air cleaner. Air suction ports are formed on a side portion and a lower portion of the main body of the air cleaner and an air discharge port is formed on an upper portion of the main body thereof.

According to this configuration, there is a problem in that a suction capacity is reduced as the contaminated air is suctioned from a limited direction, that is, from a side direction and a lower direction relative to the air cleaner. A corner portion of the case having a rectangular parallelepiped shape provides structural resistance interfering with the suction of air.

In addition, there is a problem that an air cleaning function is limited as purified air does not flow to a space away from the air cleaner, whereas air around the air cleaner is purified. That is, the air which is purified in the air cleaner is discharged in only one direction, that is, only in an upward direction. Further, there is a problem that a blowing capacity is limited as only one blowing fan is provided in the main body of the air cleaner.

BRIEF DESCRIPTION OF THE DRAWINGS

Embodiments will be described in detail with reference to the following drawings in which like reference numerals refer to like elements, and wherein.

DETAILED DESCRIPTION

Figure 1:
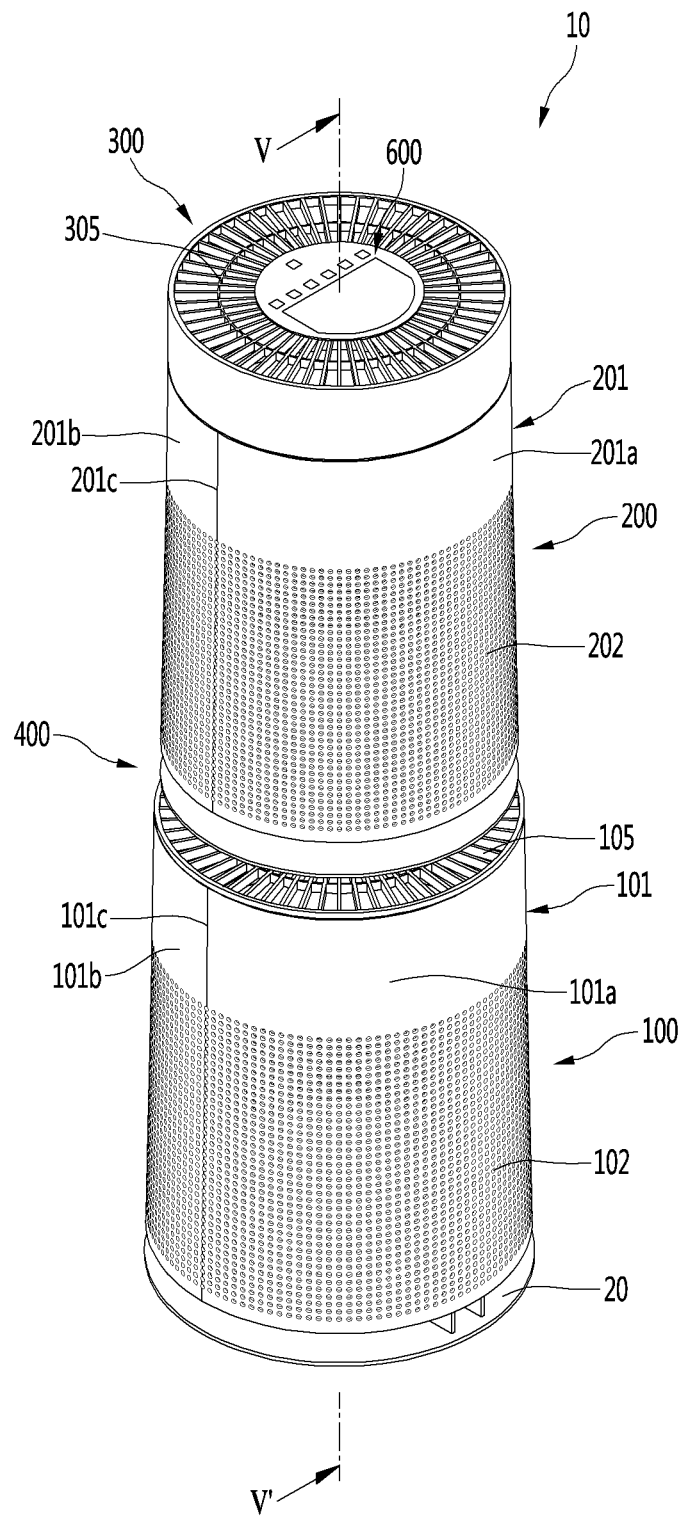
FIG. 1 is a perspective view of an air cleaner according to an embodiment.

Hereinafter, embodiments will be described in detail with reference to the illustrative drawings. Regarding the reference numerals assigned to the components in the drawings, it should be noted that the same components may be designated by the same reference numerals, wherever possible, even though they are shown in different drawings. Also, in the description of embodiments, specific description of known related configuration or functions may be omitted when it is deemed that such description may cause ambiguous interpretation of the present invention.

Also, in the description of embodiments, terms such as first, second, A, B, (a), (b) or the like may be used herein when describing components. Each of these terminologies is not used to define an essence, order or sequence of a corresponding component but used merely to distinguish the corresponding component from other component(s). In a case where it is described that any component is "connected" or "coupled" to another component, the component may be directly or indirectly connected or coupled to another component. However, it is to be understood that another component may be "connected" or "coupled" between the components.

Figure 2:
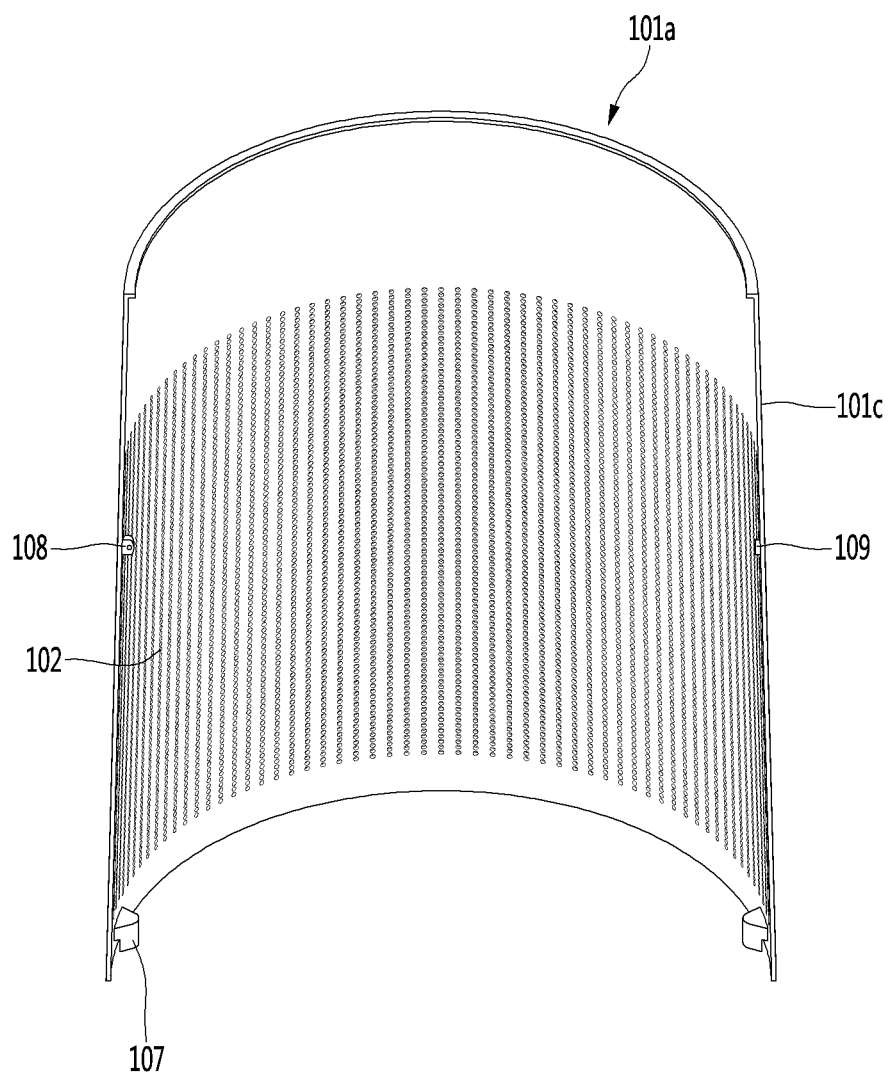
FIG. 2 is a view of a first portion of a first case of the air cleaner of FIG. 1.

FIG. 1 is a perspective view of an air cleaner according to an embodiment. FIG. 2 is a view of a first portion of a first case of the air cleaner of FIG. 1.

With reference to FIG. 1, the air cleaner 10 according to this embodiment may include blowing devices or blowers 100 and 200 that generate air flow and a flow adjusting device or adjuster 300 that adjusts a discharge direction of the air flow generated in the blowing devices 100 and 200. The blowing devices 100 and 200 may include a first blowing device 100 that generates a first air flow and a second blowing device 200 that generates a second air flow.

The first blowing device 100 and the second blowing device 200 may be provided in a vertical direction. For example, the second blowing device 200 may be provided on or at an upper side of the first blowing device 100. In this case, the first air flow is a flow of indoor air suctioned from a lower side of the air cleaner 10 and the second air flow is a flow of indoor air suctioned from an upper side of the air cleaner 10.

The air cleaner 10 may include cases 101 and 201 that form an outer appearance thereof. That is, the cases 101 and 201 may include a first case 101 that forms an outer appearance of the first blowing device 100. The first case 101 may have a cylindrical shape. An upper portion of the first case 101 may have a diameter which is less than a diameter of a lower portion thereof. That is, the first case 101 may have a truncated cone shape.

The first blowing device 100 and the second blowing device 200 may be referred to as a "first air cleaning module or cleaner 100" and a "second air cleaning module or cleaner 200", respectively, in that the first blowing device 100 and the second blowing device 200 perform a function of cleaning air in a space to be cleaned. The first blowing device 100 may be referred to as a "lower air cleaning module or cleaner" or "lower module or cleaner" in that the first blowing device 100 is provided at a lower portion of the air cleaner 10 and the second blowing device 200 may be referred to as an "upper air cleaning module or cleaner" or "upper module or cleaner" in that the second blowing device 200 is provided at an upper portion of the air cleaner 10. The flow adjusting device 300 may be referred to as "flow adjusting module or adjuster 300" or "flow control module 300".

The first case 101 may include two parts 101a and 101b which form the first case 101. The two parts 101a and 101b may include a first part 101a and a second part 101b. The first and second parts may have a same shape.

The first case 101 further may include a separation portion 101c at which the first and second parts 101a and 101b may be assembled or disassembled. The separation portion 101c may form an end portion or end of the first part 101a or an end portion or end of the second part 101b. In addition, the first case 101 may include a hinge portion or hinge provided opposite to the separation portion 101c. The two parts may be capable of relatively rotating about the hinge portion.

When at least one of the two parts is rotated, the first case 101 may be opened, and separated from the air cleaner 10. Inner components of the first blowing device 100 may be replaced or repaired by opening the first case 101.

The first case 101 may include a first suction portion or inlet 102 through which air may be suctioned in a radial direction. The first suction portion 102 may include one or more through hole formed to pass through at least a portion of the first case 101. A plurality of first suction portions 102 may be provided.

The plurality of first suction portions 102 may be evenly provided in a circumferential direction along an outer circumferential surface of the first case 101 so that air suction may be performed in any direction relative to the first case 101. That is, air may be suctioned in 360 degree directions relative to a center line that extends in the vertical direction and passes through an inside center of the first case 101.

Accordingly, a suction amount of air may be increased by the first case 101 having a cylindrical shape and the plurality of first suction portions 102 formed along the outer circumferential surface of the first case 101. Flow resistance to suctioned air may be reduced by avoiding a cube shape having edges or edge portions such as the case of the related art air cleaner.

Air which is suctioned in through the first suction portion 102 may flow substantially in the radial direction from the outer circumferential surface of the first case 101. Directions may be defined as follows. Referring to the FIG. 1, the vertical direction may refer to an axial direction and a transverse direction may refer to the radial direction. The axial direction may correspond to a central axis direction of the first fan 160 and the second fan 260, which are described hereinafter, that is, a motor shaft direction of the fan. The radial direction may refer to a direction which is perpendicular to the axial direction. The circumferential direction may refer to a virtual circle direction which is formed when rotating about the axial direction and having a distance of the radial direction as a rotational radius.

The first blowing device 100 may include a base 20 provided at a lower side of the first case 101 and placed on the ground. The base 20 may be positioned spaced apart from a lower end portion or end of the first case 101 in a downward direction. A base suction portion or inlet 103 may be formed in a space between the first case 101 and the base 20.

Air which is suctioned in through the base suction portion 103 may flow in an upward direction through a suction port 112 of a suction grill 110 (see FIG. 2), which may be provided in or at an upper side of the base 20. That is, the first blowing device 100 may include the plurality of suction portions 102 and the base suction portion 103. Air in a lower portion of the indoor space may be easily introduced to the first blowing device 100 through the plurality of suction portions 102 and the base suction portion 103. Accordingly, the suction amount of air may be increased.

A first discharge portion or outlet 105 may be formed at an upper portion of the first blowing device 100. The first discharge portion 105 may be formed on a first discharge grill 195 of a first discharge guide device or guide 190 (see, FIG. 8) which may be provided in the first blowing device 100. The first discharge guide 190 may form an outer appearance of an upper end portion or end of the first blowing device 100. Air discharged through the first discharge portion 105 may flow to the upper side in the axial direction.

The cases 101 and 201 may include a second case 201 which may form an outer appearance of the second blowing device 200. The second case 201 may have a cylindrical shape. An upper portion of the second case 201 may have a diameter which is less than a diameter of a lower portion thereof. That is, the second case 201 may have a truncated cone shape.

The second case 201 may include two parts 201a and 201b which form the second case 201. The two parts 201a and 201b may include a first part 201a and a second part 201b. The first and second parts 201a and 201b have a same shape.

The second case 201 further may include a separation portion 201c at which the first and second parts 201a and 201b may be assembled or disassembled. The separation portion 201c may form an end portion or end of the first part 201a or an end portion or end of the second part 201b. In addition, the second case 201 may include a hinge portion or hinge provided opposite to the separation portion 101c. The two parts may be capable of relatively rotating about the hinge portion.

When at least one of the two parts is rotated, the second case 201 may be opened, and separated from the air cleaner 10. Inner components of the second blowing device may be replaced or repaired by the second case 201 being opened.

A diameter of a lower end portion of the second case 201 may be less than a diameter of the upper end portion or end of the first case 101. Accordingly, in a general shape of the cases 101 and 201, a lower cross-sectional area of the cases 101 and 102 may be formed to be greater than an upper cross-sectional area. That is, the diameter of each of the cases 101 and 102 may be configured to be gradually increased toward the downward direction from the upper end portion or end thereof.

The second case 201 may include a second suction portion or inlet 202 through which air may be suctioned in the radial direction. The second suction portion 202 may include one or more through hole formed to pass through at least a portion of the second case 201. A plurality of the second suction portion 202 may be provided.

The plurality of second suction portions 202 may be evenly provided in the circumferential direction along an outer circumferential surface of the second case 201 so that air suction may be performed in any direction relative to the second case 201. That is, air may be suctioned in 360 degree directions relative to a center line that extends in the vertical direction and passes through an inside center of the second case 201.

Accordingly, a suction amount of air may be increased by the second case 201 having a cylindrical shape and the plurality of second suction portions 202 formed along the outer circumferential surface of the second case 201. Flow resistance to suctioned air may be reduced by avoiding a cube shape having an edge portions such as the case of the related are air cleaner. Air which is suctioned in through the second suction portion 202 may flow substantially in the radial direction from the outer circumferential surface of the second case 201.

Any one of the two parts which form the first case 101 or the second case 201 may have a semi-cylindrical shape or a semi-cone shape (a shape which is ½ of a truncated cone shape). If two parts having this shape are coupled, the two parts may form the first or second case 101 or 201 having a cylindrical shape or a cone shape (truncated cone shape).

FIG. 2 illustrates, as an example, a configuration of the first part 101a of the first case 101. A shape of the first part 201a of the second case 201 may be identical in shape to the first part 101a, and therefore, repetitive description has been omitted. In addition, an entire shape of each of the first and second parts 201a and 201b of the second case 201 may be the same or similar to the shape of the first part 101a of the first case 101; however, a size of each of the first and second parts 201a and 201b may be greater than the size of the first part 101a. Thus, the description regarding to the first part 101a of the first case 101 may be applied to the first and second parts 201a and 201b of the second case 201.

The first part 101a of the first case 101 may include a fastening portion 108 which may fasten the first part 101a and the second part 101b. The fastening portion 108 of the first part 101a may be coupled to a fastening portion of the second part 101b. The coupled fastening portions may form the hinge portion of the first and second parts 101a and 101b.

The first part 101a may include a magnet member or magnet 109 which enables the first and second parts 101a and 101b to be detachably coupled to each other. The magnet member 109 may be installed or provided at the separation portion 101c. The magnet member 109 of the first part 101a may be coupled to a magnet member or magnet of the second part 101b. In order to open the first case 101, the magnet 109 of the first part 101a and the magnet of the second part 101b may be separated from each other.

A locking projection 107, which enables the first part 101a to be supported on an outside of the first filter 120, may be provided at a lower portion of the first part 101a. The locking projection 107 may protrude in the radial direction from an inner circumferential surface of the first part 101a. For example, the locking projection 107 may be locked to a locking portion 131b (see FIG. 6), which may be provided at a lower portion of a first filter frame 130. The locking projection 107 may be provided at both sides of the first part 101a.

The locking projection may be provided for the first and second parts 201a and 201b, which form the second case 201. However, a distance from an inner circumferential surface of the second case 201 to a second filter frame 230 may be greater than a distance from an inner circumferential surface of the first case 101 to the first filter frame 130. In addition, the first and second filter frames 130 and 230 may have a same shape and size. Therefore, a length in the radial direction of the locking projection provided for the first and second parts 201a and 201b of the second case 201 may be longer than a length in the radial direction of the locking projection 107 provided to the first and second parts 101a and 101b of the first case 101.

The air cleaner 10 may include a dividing device or divider 400 provided between the first blowing device 100 and the second blowing device 200. By the dividing device 400, the second blowing device 200 may be positioned at the upper side of the first blowing device 100 spaced apart therefrom. The dividing device 400 includes a dividing plate 430 which is formed sufficiently long in the outside in the radial direction from the upper side of the first blowing device 100. By the dividing plate 430, air which is discharged from the first blowing device 100 can be prevented from being sucked to the second blowing device 200.

The flow adjusting device 300 may be provided at an upper side of the second blowing device 100. An air flow path of the second blowing device 100 may communicate with an air flow path of the flow adjusting device 300. The air passing through the second blowing device 100 may be discharged through a second discharge portion or outlet 305 to the outside via the air flow path of the flow adjusting device 300. The second discharge portion 305 may be provided on or at an upper end portion of the flow adjusting device 300.

Figure 16:
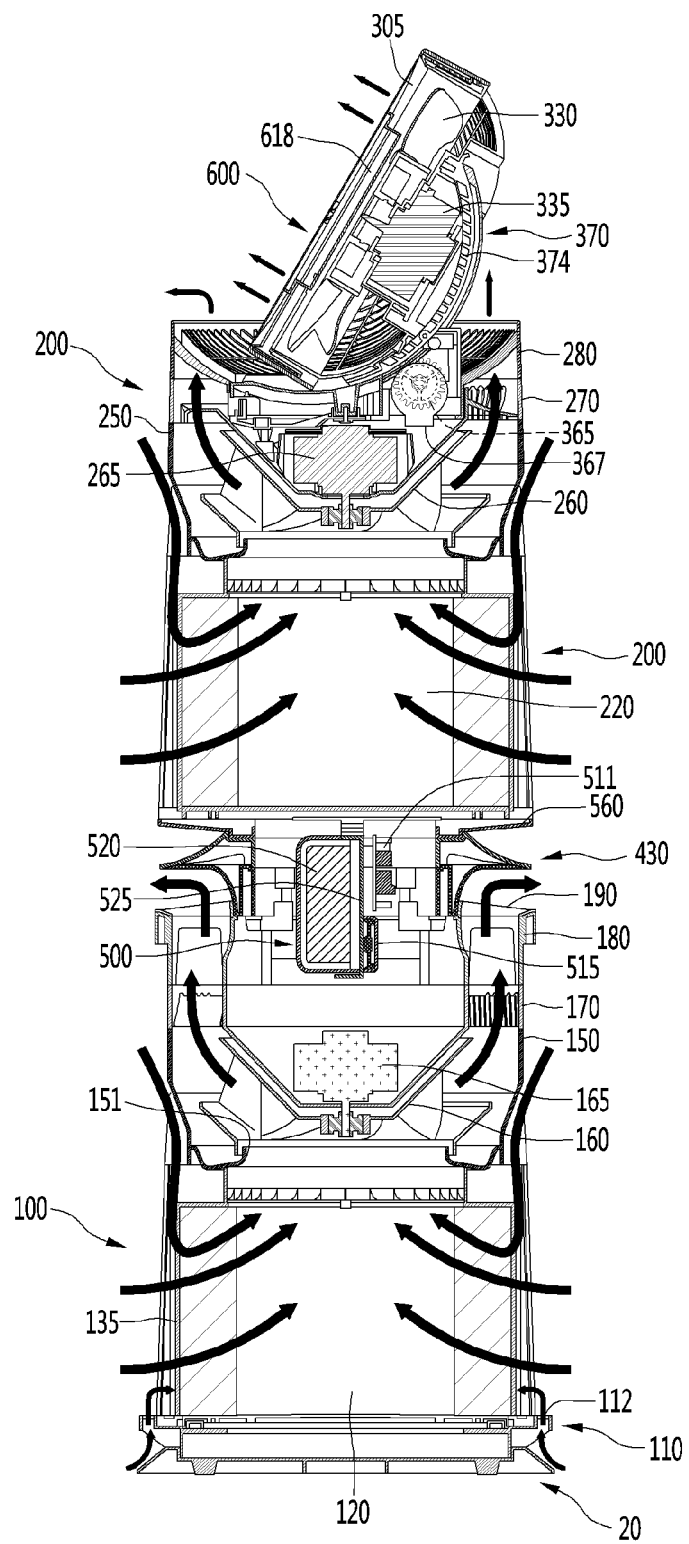

The flow adjusting device 300 may be movable. That is, the flow adjusting device 300 may be movable between a laid-out state (first position), as illustrated in FIG. 1, or an inclined erected state (second position), as illustrated in FIG. 16. In addition, a display device or display 600 that displays operation information of the air cleaner may be provided at an upper portion of the flow adjusting device 300. The display device 600 may be movable together with the flow adjusting device 300.

Figure 3:
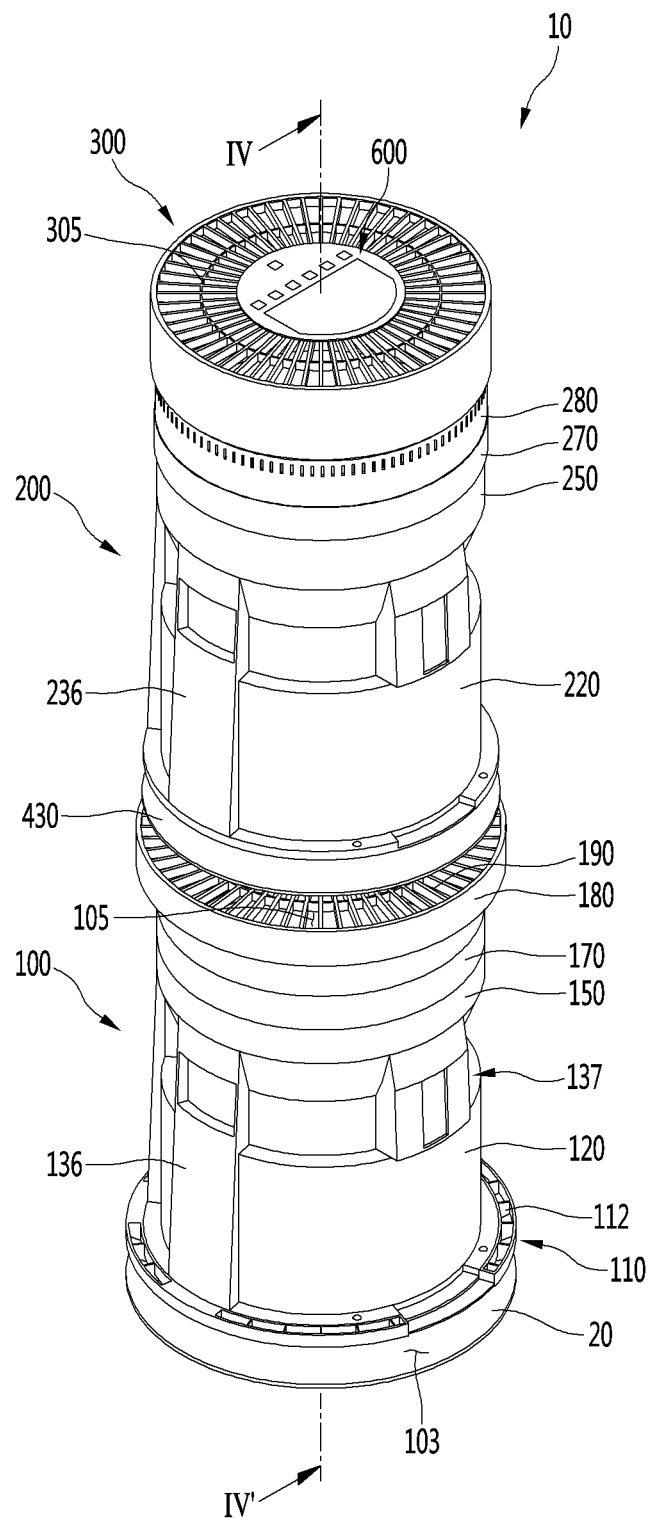
FIG. 3 is a perspective view illustrating an internal configuration of the air cleaner of FIG. 1.
Figure 4:
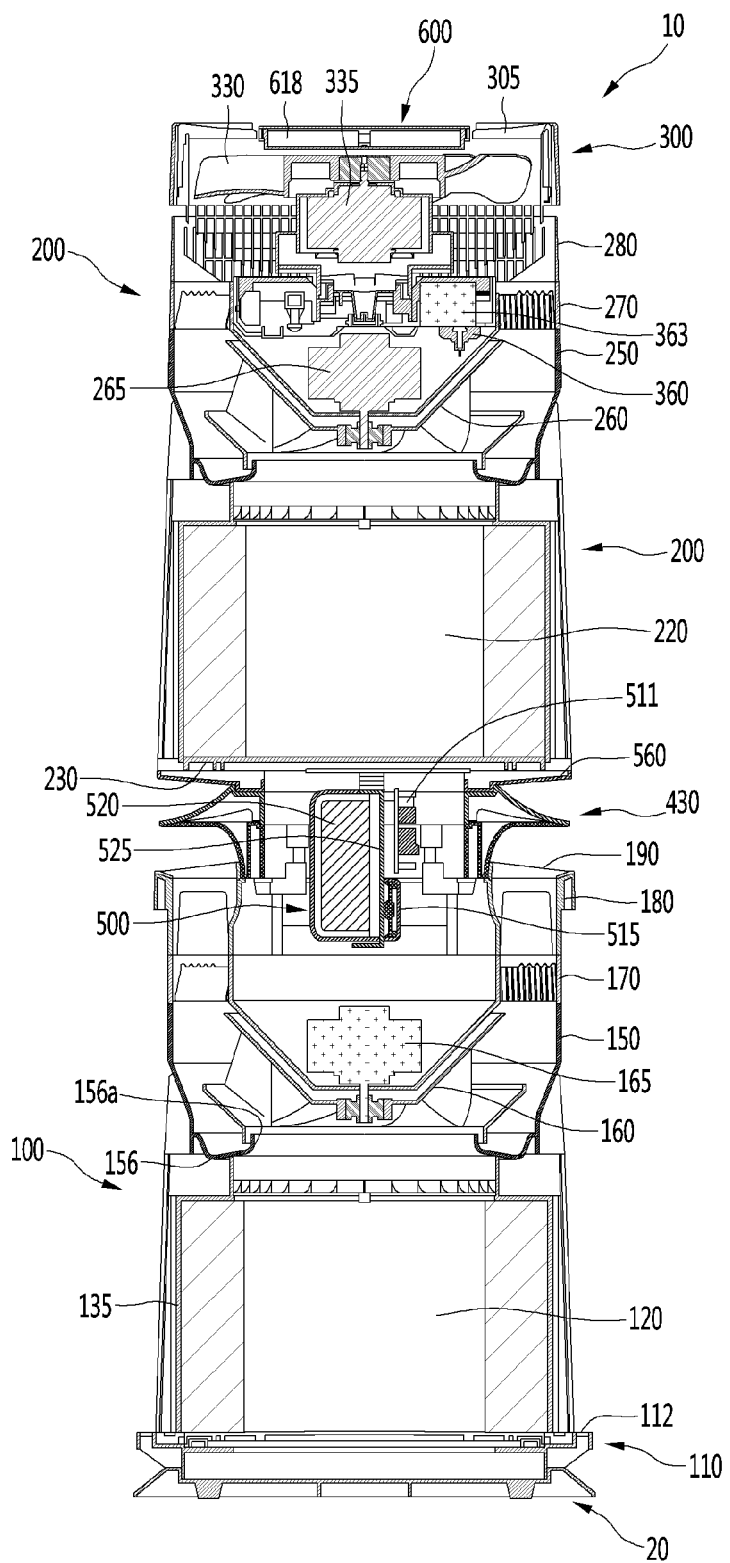
FIG. 4 is a cross-sectional view, taken along line IV-IV' of FIG. 3.
Figure 5:
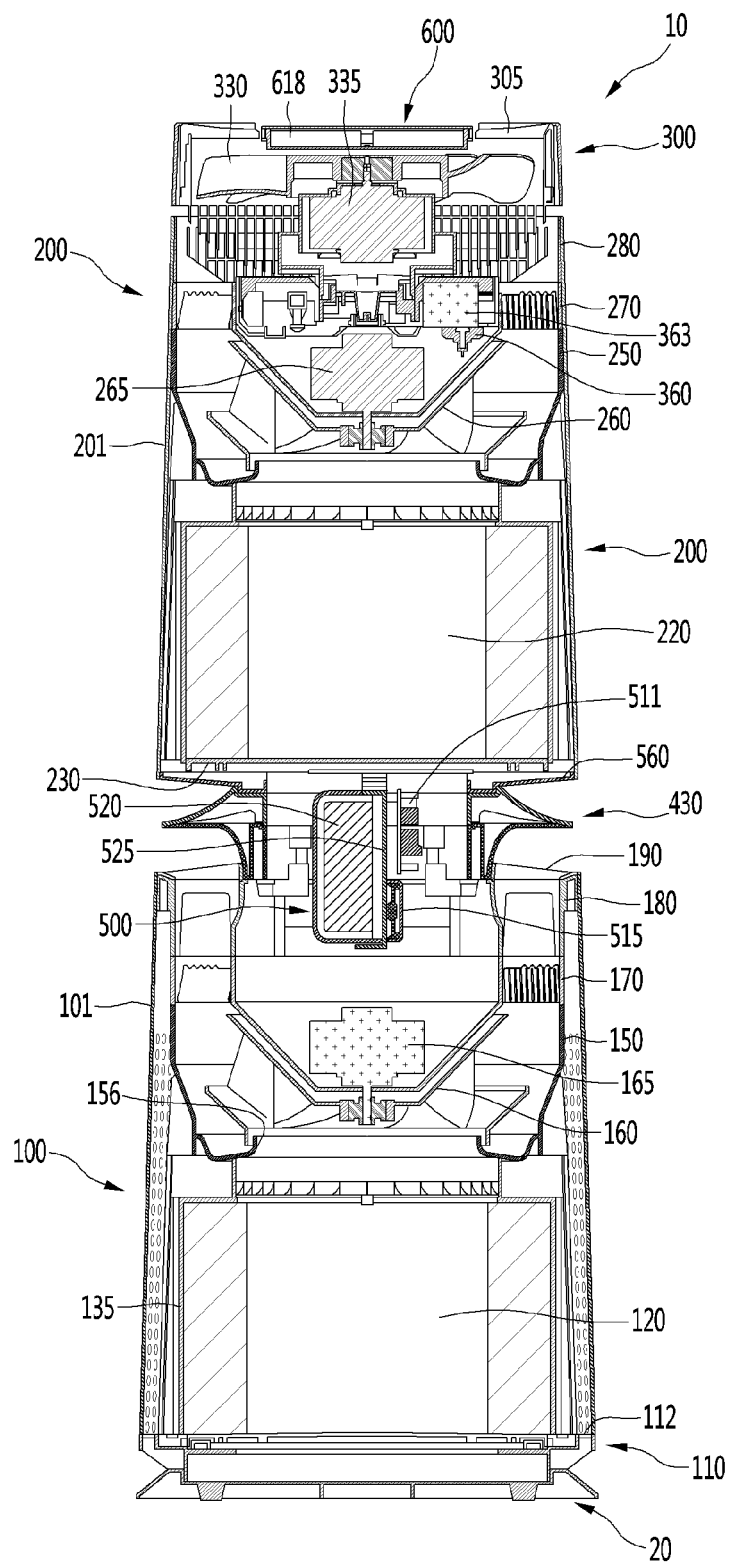
FIG. 5 is a cross-sectional view, taken along line V-V' of FIG. 1.
Figure 6:
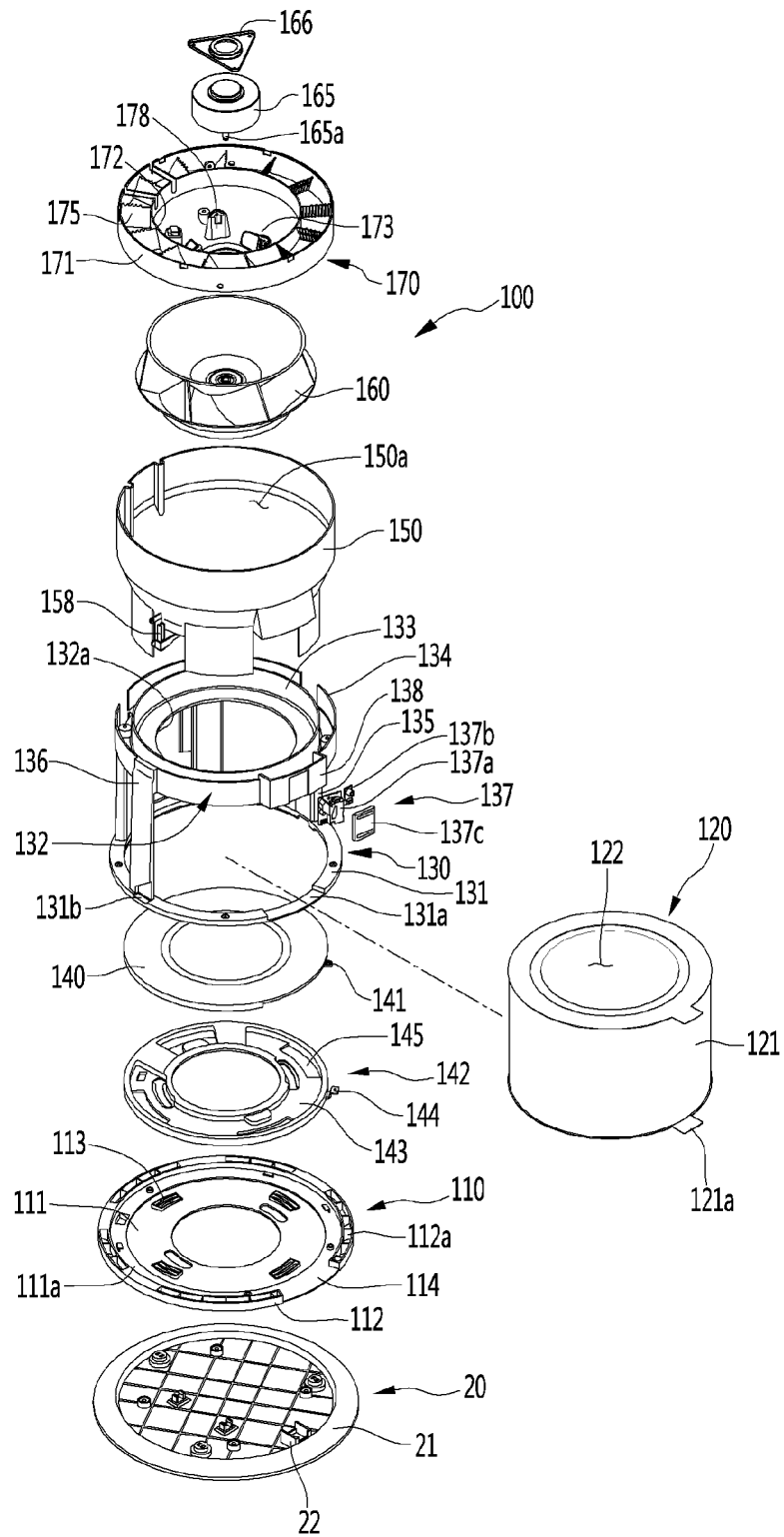
FIG. 6 is an exploded perspective view of a first blowing device of the air cleaner of FIG. 1.
Figure 7:
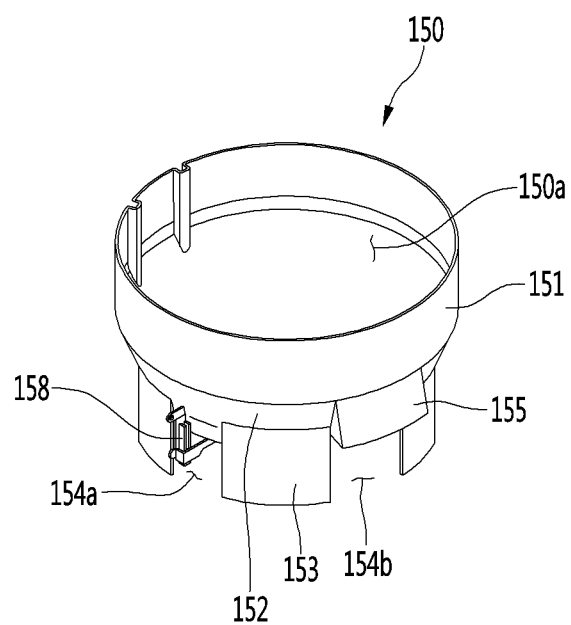
FIG. 7 is a perspective view of a fan housing of the air cleaner of FIG. 1.
Figure 8:
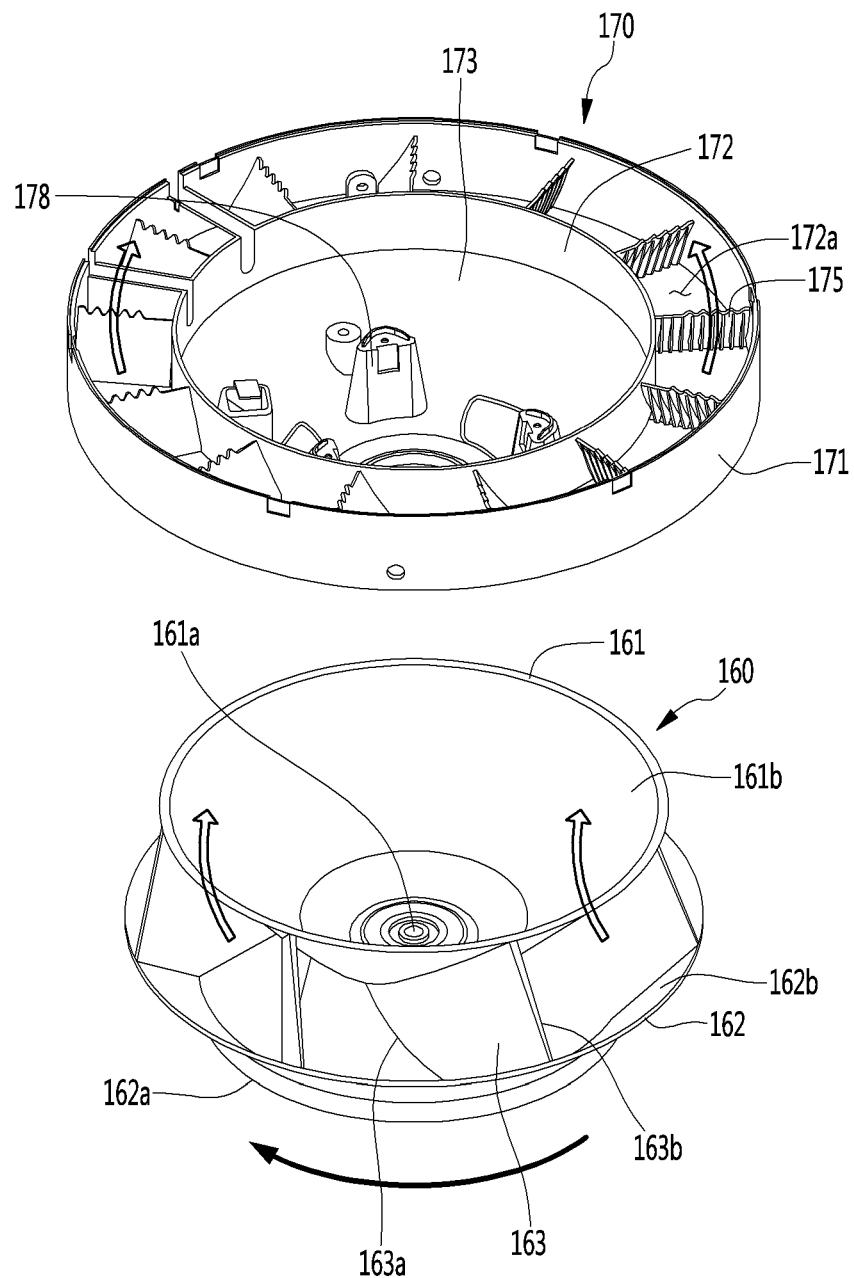
FIG. 8 is an exploded perspective view of a first fan and a first air guide of the air cleaner of FIG. 1.
Figure 9:
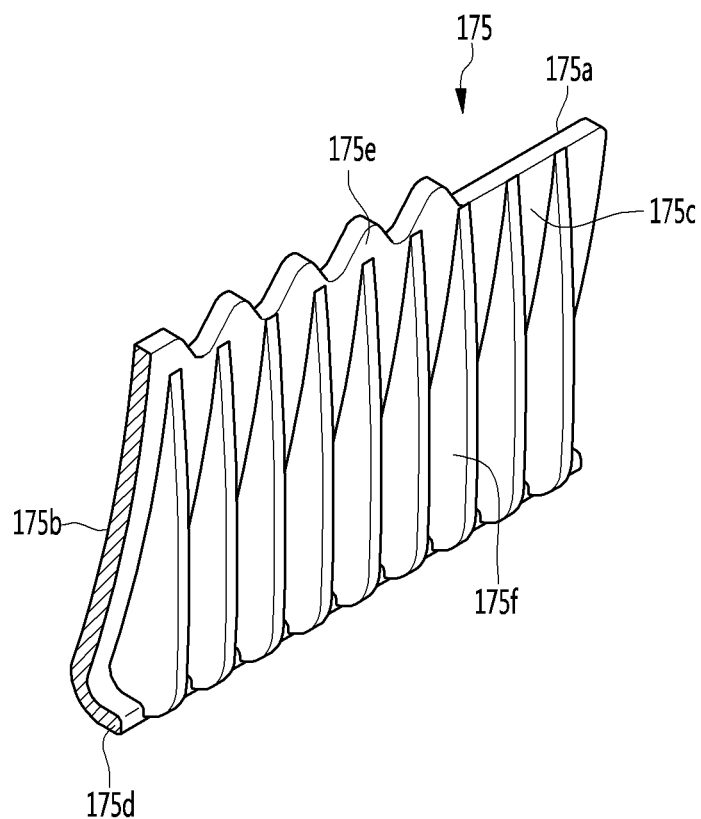
FIG. 9 is a perspective view of a guide rib of the air cleaner of FIG. 1.

FIG. 3 is a perspective view illustrating an internal configuration of the air cleaner of FIG. 1. FIG. 4 is a cross-sectional view, taken along line IV-IV' of FIG. 3. FIG. 5 is a cross-sectional view, taken along line V-V' of FIG. 1. FIG. 6 is an exploded perspective view of a first blowing device of the air cleaner of FIG. 1. FIG. 7 is a perspective view of a fan housing of the air cleaner of FIG. 1. FIG. 8 is an exploded perspective view of a first fan and a first air guide of the air cleaner of FIG. 1. FIG. 9 is a perspective view of a guide rib of the air cleaner of FIG. 1.

Referring to FIGS. 3 to 9, the base 20 and the suction grill 110 which may be disposed or provided on or at an the upper side of the base 20 may be included in the first blowing device 100 according to the embodiment. The base 20 may include a base main body 21, which may be placed on the ground, and a base projecting portion or projection 22 that projects from the base main body 21 in the upward direction and on which the suction grill 110 may be placed. The base projecting portion 22 may be provided at both sides of the base 20.

The base main body 21 and the suction grill 110 may be spaced apart from each other by the base projecting portion 22. The base suction portion 103 which forms a suction space of air may be included between the base 20 and the suction grill 110.

The suction grill 110 may include a grill main body 111 having a substantially ring shape and a rim portion or rim 110a that protrudes from an outer circumferential surface of the grill main body 111 in the upward direction. By the configuration of the grill main body 111 and the rim portion 111a, the suction grill 110 may have a stepped structure.

The suction grill 110 may include a suction portion or inlet 112 formed on the rim portion 111a. The suction portion 112 may protrude along a circumference of the rim portion 111a in the upward direction and extend in a circumferential direction. In addition, a plurality of suction holes 112a may be formed in the suction portion 112. The plurality of suction holes 112a may communicate with the base suction portion 103.

Air suctioned in through the plurality of suction holes 112a and the base suction portion 103 may pass through a first filter member or filter 120. The first filter may have a cylindrical shape and a filter surface that filters air. The air passing through the plurality of suction holes 112a may be introduced to an inside portion of the first filter 120 by passing through an outer circumferential surface of the cylindrical first filter 120. In addition, the first case 101 may be supported on or at an upper portion of the suction portion 112.

The suction grill 110 may further include a movement guide portion or guide 113 that protrudes from a top surface of the grill main body 111 in the upward direction to guide movement of the first filter 120 in the upward or downward direction. The movement guide 113 may be configured to have a shape further protruding in the circumferential direction from the top surface of the grill main body 111. That is, the movement guide 113 may have an inclined surface that protrudes in the circumferential direction.

A plurality of movement guides 113 may be provided to be spaced apart from each other in the circumferential direction. For example, as shown in FIG. 4, four movement guides 113 may be provided. However, a number of the movement guides 113 is not limited thereto.

The grill main body 111 may further include a groove portion or groove 114 which provides a space in which a handle 144 described hereinafter may be movable. The groove 113 forms at least a portion of the grill main body 111, and may be a portion at which the suction portion 112 is not formed in the rim portion of the grill main body 111.

The first blowing device 100 may include a lever device or lever 142, which may be provided on or at an upper side of the suction grill 110 and which may be operable by a user. The lever device 142 may be rotatable in the circumferential direction.

The lever device 142 may include a lever main body 143, which may have a substantially ring shape and be rotatable. In addition, a plurality of cut-out portions or cut-outs disposed or provided at positions corresponding to the plurality of movement guides 113 may be formed in the lever main body 143. The plurality of cut-out portions 145 may be through holes formed in the lever main body 143.

The plurality of cut-out portions 145 may be arranged in the circumferential direction of the lever main body 143 spaced apart from each other. In addition, each of the cut-out portions 145 may be rounded with a predetermined curvature in the circumferential direction, corresponding to the curvature of an outer circumferential surface of the lever main body 143.

The lever device 142 may be supported on the upper surface of the grill main body 111. If the lever device 142 is supported by the grill main body 111, the plurality of movement guides 113 may be inserted into the plurality of cut-out portions 145. The plurality of movement guides 113 may protrude from the plurality of cut-out portions 145 in the upward direction by passing through the plurality of cut-out portions 145.

A length of each of the cut-out portions 145 may be formed longer than a length of the movement guide 113. Thus, the lever device 142 may rotate in a state in which the movement guide 113 is inserted into the cut-out portion 145. In addition, one end portion or end of the movement guide 113 may interfere with one end portion or end of the cut-out portion 145 in a process in which the lever device 142 rotates in one direction, and the other end portion or end of the movement guide 113 may interfere with the other end portion or end of the cut-out portion 145. A second handle 144 may be provided at the outer circumferential surface of the lever main body 143.

A supporting device 140 that supports the first filter 120 may be provided on an upper side of the lever device 142. The supporting device 140 may include a first handle 141 coupled to the second handle 144. A user may grasp the first and second handles 141 and 144 and then rotates the lever main body 143 and the supporting device 140 in a clockwise direction or in a counterclockwise direction.

The lever device 142 may support a lower surface of the supporting device 140. A support projecting portion or projection (not shown), which may be in contact with the movement guide 113, may be provided on the supporting device 140. The support projecting portion may protrude downward from the lower surface of the supporting device 140, and may be provided at a position corresponding to the movement guide 113. In addition, a shape of the support projecting portion may correspond to a shape of the movement guide 113, and the support projecting portion may include an inclined surface formed to further protrude in the circumferential direction.

A direction in which the movement guide 113 gradually projects and a direction in which the support projecting portion gradually projects may be opposite to each other. For example, when the direction in which the movement guide 113 gradually projects is the counterclockwise direction, the direction in which the support projecting portion gradually projects may be clockwise direction.

The support projecting portion may be disposed or provided at a position corresponding to the cut-out portion 145. That is, the movement guide 113 and the support projecting portion may be disposed or provided at a position at which they are inserted into the cut-out portion 145.

The lever device 142 and the supporting device 140 may rotate together. In the rotation process, the movement guide 113 and the support projecting portion may interfere with each other. If a lower portion of the support projecting portion and an upper portion of the movement guide 113 are in contact with each other, the lever device 142 and the supporting device 140 may be lifted in the upward direction.

In addition, the first filter 120 supported by the supporting device 140 may be in a state in which the first filter 120 is coupled to the first blowing device 100 while moving in the upward direction.

On the other hand, if the lower portion of the support projecting portion and the upper portion of the movement guide 113 are in contact with each other or if inference between the support projecting portion and the movement guide 113 is released, the lever device 142 and the supporting device 140 may move downward. In addition, the first filter 120 supported by the supporting device 140 may be in a state (released state) in which the first filter 120 is separable from the first blowing device 100.

The first filter 120 may have a cylindrical shape having an open upper portion. The first filter 120 may include a filter main body 121, which may have a cylindrical filter, an inside of which may be empty, and a filter hole 122 formed to be open at an upper end portion or end of the filter main body 121. A filter grasping portion or grasp 121a may be provided at an upper or lower portion of the filter main body 121. Air may be introduced to the inside of the filter main body 121 through an outer circumferential surface of the film main body 121, and may be discharged from the first filter 120 through the filter hole 122.

The first blowing device 100 may further include a first filter frame 130, which may form a mounting space for the first filter 120. More specifically, the first filter frame 130 may include a first frame 131, which may form a lower portion of the first filter frame 130 and a second frame 132, which may form an upper portion of the first filter frame 130.

The first frame 131 may include a frame depression portion or depression 131a having a downwardly depressed shape. The frame depression portion 131a may be configured such that at least a portion of the first frame 131 is depressed. The frame depression portion 131a may be formed at a position corresponding to the groove portion 114 of the suction grill 110. The groove portion 114 and the frame depression portion 131a may provide a space portion or space in which the first and second handles 141 and 144 may be movable. The first and second handles 141 and 144 may be located in the space portion, to rotate in the clockwise direction or in the counterclockwise direction.

In addition, the locking portion 131b to which the locking projection 107 of the first case 101 may be coupled may be formed on the first frame 131. The locking portion 131b may be formed at the outside of a first filter supporting portion 135.

The second frame 132 may have a ring shape and surround an upper portion of the first filter 120. The second frame 132 may be spaced apart from the first frame 131 in the upward direction.

The ring-shaped inside portion space of the second frame 132 may form a frame hole 132a. The frame hole 132a may communicate with the filter hole 122 of the first filter 120. That is, the frame hole 132a may form at least a portion of the flow path of air which passes through the first filter frame 130, and air which is discharged through the filter hole 122 of the first filter 120 may be introduced to a first fan housing 150 through the frame hole 132a. That is, the first filter 120 may be installed or provided at a suction side of the first fan 160.

The upper portion of the second frame 132 may support the first fan housing 150. A first fan introducing portion 156 that guides introduction of air to the inside portion of the first fan housing 150 may be included in the lower portion of the first fan housing 150. The first fan introducing portion 156 may extend to the inside in the radial direction of a third main body 153. In addition, a fan introducing hole 156a, which may communicate with the frame hole 132a, may be formed in the first fan introducing portion 156.

That is, the first fan housing 150 may be coupled to the upper side of the second frame 132, and the fan introducing hole 156a and the frame hole 132a may be aligned in the vertical direction. According to this configuration, air which passes through the frame hole 132a may be introduced to the inside of the first fan housing 150 through the fan introducing hole 156a, and it is possible to prevent the air from leaking outside of the first fan housing 150. In addition, it may prevent a finger, for example, a user from being put into the inside of the first fan housing 150 when the first filter 120 is separated by the grill being provided in the first fan introducing portion 156.

The second frame 132 may include a frame inner wall 133, and a frame outer wall 134 that surrounds the frame inner wall 133. Each of the frame inner wall 133 and the frame outer wall 134 may have a ring shape. In addition, the frame hole 132a may be an inside space of the frame inner wall 133.

An inner circumferential surface of the frame outer wall 134 may be spaced apart from an outer circumferential surface of the frame inner wall 133. In addition, at least a portion of the first fan housing 150 may be located in a space between the inner circumferential surface of the frame outer wall 134 and the outer circumferential surface of the frame inner wall 133. That is, at least a portion of the first fan housing 150 may be inserted into the space (hereinafter, referred to as a "housing insertion portion") between the inner circumferential surface of the frame outer wall 134 and the outer circumferential surface of the frame inner wall 133.

The first filter frame 130 may further include a first filter supporting portion or support 135 that extends from the first frame 131 to the second frame 132 in the upward direction. The first frame 131 and the second frame 132 may be spaced apart from each other by the first filter supporting portion 135. A plurality of first filter supporting portions 135 may be provided and the plurality of the first filter supporting portions 135 may be arranged in the circumferential direction, and thus, may be connected to rim portions or rims of the first frame 131 and the second frame 132. A mounting space of the first filter 120 may be defined by the plurality of first filter supporting portions 135 and the first frame 131 and the second frame 132.

A sensor device 137 may be installed or provided in or on the first filter frame 130. The sensor device 137 may include a dust sensor 137a that senses an amount of dust in the air and a gas sensor 137b that senses an amount of gas in the air. In addition, the sensor device 137 may include a sensor cover 137c that shields the dust sensor 137a and the gas sensor 137b.

The dust sensor 137a and the gas sensor 137b may be supported by the second frame 132 of the first filter frame 130. The second frame 132 may include a sensor mounting portion 138, on which the sensor device 137 may be installed or provided. The sensor mounting portion 138 may protrude from the outer circumferential surface of the second frame 132.

The first filter 120 may be detachably mounted in the mounting space. The first filter 120 may have a cylindrical shape and air may be introduced through the outer circumferential surface of the first filter 120. Impurities, such as fine dust in air, may be filtered in a process of passing through the first filter 120.

The air may be introduced from any direction relative to the first filter 120, by the first filter 120 having the cylindrical shape. Accordingly, a filtering area of air may be increased.

The mounting space may have a cylindrical shape corresponding to the shape of the first filter 120. The first filter 120 may be slidably introduced toward the mounting space in a mounting process. In contrast, the first filter 120 may be slidably withdrawn from the mounting space in a separating process.

That is, when the first and second handles 141 and 144 are operated in a state in which the first filter 120 is located on the upper surface of the supporting device 140, the first filter 120 may be in a released position with the first filter 120 being moved in the downward direction. The first filter 120 may be slid to the outside in the radial direction and may be separated from the mounting space.

In contrast, when separated from the mounting space the first filter 120 may be slid toward the mounting space to the inside in the radial direction, supported on the upper surface of the supporting device 140, and thus, may be in close contact upwardly by an operation of the first and second handles 141 and 144. At this time, the first filter 120 is in a coupling position. A first supporting portion cover 136 may be coupled with the outside of the first filter supporting portion 135.

The first blowing device 100 further may include a first fan housing 150 which may be installed or provided on or at an outlet side of the first filter 120. Referring to FIG. 7, the first fan housing 150 may include a housing main body 151, 152, and 153, which may form a housing space portion or space 150a in which the first fan 160 may be accommodated. The housing main body 151, 152, and 153 may be supported by the first filter frame 130.

The housing main body 151, 152, and 153 may be stepped such that its diameter is changed. The housing main body 151, 152, and 153 may include a first main body 151, which has a set or predetermined first diameter (hereinafter, referred to as a "first set diameter") and a substantially cylindrical shape. The first main body 151 may form an upper portion of the housing main body 151, 152, and 153.

The housing main body 151, 152, and 153 may further include a second main body 152 that extends at an incline from the first main body 151. For example, the second main body 152 may extend at an incline such that its diameter decreases in the downward direction from the lower portion of the first main body 151.

The housing main body 151, 152, and 153 may further include the third main body 153 the extends in the downward direction from the second main body 152 and having a set second diameter (hereinafter, referred to as a "second set diameter"). The second set diameter may be smaller than the first set diameter.

According to the configuration of the first, second, and third main bodies 151, 152, and 153, the housing main body 151, 152, and 153 may be configured such that its lower diameter is smaller than its upper diameter. Therefore, a distance between an outer surface of the first fan housing 150 and an inner circumferential surface of the first case 101 which surrounds the first fan housing 150 may be differently formed in the vertical direction.

The housing main body 151, 152, and 153 may include a housing cut-out portion or cut-out 154a and 154b. The housing cut-out portion 154a and 154b may be formed by cutting out at least a portion of the third main body 153. For example, the housing cut-out portion 154a and 154b may be formed by cutting out by a predetermined height in the upward direction from the lower end portion of the third main body 153.

The housing cut-out portion 154a and 154b may include a first cut-out portion or cut-out 154a which may be formed at a position corresponding to the first filter supporting portion 135 to support the first filter supporting portion 135. The first filter supporting portion 135 or the first supporting portion cover 136 may be located in the first cut-out portion 154a.

The housing cut-out portion 154a and 154b may include a second cut-out portion or cut-out 154b which may be formed at a position corresponding to the sensor mounting portion 138 to support the sensor mounting portion 138. The sensor mounting portion 138 may be located in the second cut-out portion 154b. In addition, a sensor supporting portion or support 155, which may be supported by the sensor mounting portion 138, may be disposed or provided on or at an upper side of the second cut-out portion 154b. An installation space portion or space, in which the sensor device 137 may be installed or provided may be defined by the sensor mounting portion 138 and the sensor supporting portion 155.

The third main body 153 may be located to be inserted into the housing insertion portion, which may be formed in the second frame 132. In summary, the third main body 153 may be inserted into the housing insertion portion, and the housing cut-out portion 154a and 154b may support the first filter frame 135 and the upper portion of the sensor mounting portion 138, so that the first filter frame 130 and the first fan housing 150 may be stably coupled to each other.

The first blowing device 100 may further include an ionizer 158 that removes or sterilizes smell particles in the air. The ionizer 158 may be coupled to the first fan housing 150 and be capable of acting on the air which flows inside of the first fan housing 150. For example, the first ionizer 158 may be located in the first cut-out portion 154a, and may be coupled to the third main body 153.

The sensor device 137 and the ionizer 158 may also be installed or provided in a second blowing device 200 described hereinafter. For example, the sensor device 137 and the ionizer 158 may be installed or provided in one of the first blowing device 100 or the second blowing device 200.

The first fan 160 may be located on or at an the upper side of the first fan introducing portion 151. For example, the first fan 160 may include a centrifugal fan that introduces air in the axial direction and then discharges air to the upper side in the radial direction.

The first fan 160 may include a hub 161 to which a rotational shaft 165a of a first fan motor 165, which may be a centrifugal fan motor, may be coupled, a shroud 162 which may be disposed or provided in a state of being spaced apart from the hub 161, and a plurality of blades 163, which may be disposed or provided between the hub 161 and the shroud 162. The first fan motor 165 may be coupled to the upper side of the first fan 160.

The hub 161 may have a bowl shape, a diameter of which may be gradually reduced in the downward direction. The hub 161 may include a shaft coupling portion to which the rotational shaft 165a may be coupled and a first blade coupling portion that extends at an incline from the shaft coupling portion in the upward direction.

The shroud 162 may include a lower end portion or lower end, on or at which a shroud suction port 162a, into which air having passed through the first fan introducing portion 151 may be suctioned, may be formed and a second blade coupling portion that extends from the lower end portion in the upward direction.

A first surface of each blade 163 may be coupled to the first blade coupling portion of the hub 161 and a second surface thereof may be coupled to the second blade coupling portion of the shroud 162. The plurality of blades 163 may be disposed or provided spaced apart in a circumferential direction of the hub 161.

Each blade 163 may include a leading edge 163a, which forms a side end portion or side end, to which air is introduced, and a trailing edge 163b, which forms a side end portion or side end, from which air is output. The air having passed through the first filter 120 may be introduced to the first fan housing 150 through the first fan introducing portion 151 with the air flowing in the upward direction. The air may flow in the axial direction of the first fan 160, may be introduced to the first leading edge 163a, and may be output to the trailing edge 163b via the blade 163. The trailing edge 163b may extend at an inclined to the outside with respect to the axial direction in the upward direction corresponding to a flow direction of air so that the air which is output through the trailing edge 163b is capable of flowing to the upper side in the radial direction.

Reference to FIG. 5, the first blowing device 100 may further include a first air guide device or guide 170 which may guide a flow of air having passed through the first fan 160 by being coupled to the upper side of the first fan 160. The first air guide 170 may include an outer wall 171 having a cylindrical shape and an inner wall 172 positioned on or at an inside of the outer wall 171 and having a cylindrical shape. The outer wall 171 may be disposed or provided to surround the inner wall 172. A first air flow path 172a, through which air may flow, may be formed between an inner circumferential surface of the outer wall 171 and an outer circumferential surface of the inner wall 172.

The first air guide 170 may include a guide rib 175 which may be disposed or provided on or in the first air flow path 172a. The guide rib 175 may extend from the outer circumferential surface of the inner wall 172 to the inner circumferential surface of the outer wall 171. A plurality of guide ribs 175 may be disposed or provided spaced apart from each other. The plurality of guide ribs 175 may guide the air introduced to the first air flow path 172a of the first air guide 170 via the first fan 160 in the upward direction.

The guide rib 175 may extend at an incline from a lower portion of the outer wall 171 and the inner wall 172 in the upward direction. For example, the guide rib 175 may be rounded, and thus, guide air so that it flows at an incline in the upward direction.

That is, with reference to FIG. 9, the guide rib 175 may include a rib main body 175a, which may extend rounded in the upward direction. The rib main body 175a may include a positive pressurizing surface 175b which faces in a direction in which an air flow approaches and a negative pressuring surface 175c which is opposite to the positive pressurizing surface 175b. The positive pressurizing surface 175b may have a concave shape and the negative pressurizing surface 175c may have a convex shape.

The rib main body 175a may include a leading edge 175d which forms a side end portion or side end, to which air may be introduced, and a trailing edge 175e which forms a side end portion or side end, to which air may be discharged. The leading edge 175d may be rounded and bent from the positive pressurizing surface 175b toward the negative pressurizing surface 175c. According to this configuration, a portion of air which is introduced via the leading edge 175d may be guided to the positive pressurizing surface 175b and the rest of the air may be guided to the negative pressurizing surface 175c. Air which flows to the negative pressurizing surface 175c may pass by a plurality of projecting portions 175f.

The plurality of projecting portions 175f may project from the negative pressurizing surface 175c and may extend from the leading edge 175d toward the trailing edge 175e. The projecting portion 175f may have an airfoil shape a projecting height of which may be gradually reduced from the leading edge 175d toward the trailing edge 175e. Generation of a vortex on the negative pressurizing surface 175c may be prevented, and thus, air may easily flow toward the upper side, due to the plurality of projecting portions 175f formed on the negative pressurizing surface 175c.

The trailing edge 175e may have a saw tooth shape having peaks and valleys which may be repeated in the radial direction. According to this configuration, a difference between times at which air is output from the trailing edge 175e, that is, air is output from the peaks and valleys from each other may be generated, and thus, generation of noise may be reduced.

The first air guide 170 may further include a motor accommodating portion 173 that extends from the inner wall 172 to the lower side, and thus, accommodates the first fan motor 165. The motor accommodating portion 173 may have a bowl shape, a diameter of which may be gradually reduced in the downward direction. A motor coupling portion 166 may be provided on or at one side of the first fan motor 165 to fix the first fan motor 165 to the first air guide 170. A shape of the motor accommodating portion 173 may correspond to the shape of the hub 161. The motor accommodating portion 173 may be inserted into the hub 161.

The first fan motor 165 may be supported to or at an upper side of the motor accommodating portion 173. The rotational shaft 165a of the first fan motor 165 may extend from the first fan motor 165 in the downward direction and be coupled to the shaft coupling portion 161a of the hub 161 through the lower surface portion of the motor accommodating portion 173.

In addition, a motor coupling portion 166 may be provided on or at an upper side of the first fan motor 165. The motor coupling portion 166 may guide the first fan motor 165 to be fixed to the air guide 170.

The second blowing device 200 may include a second filter member or filter 220, a second filter frame 230, a second fan housing 250, a second fan 260, and a second fan motor 265. These components may be the same as similar to the first filter 120, the first filter frame 130, the first fan housing 150, the first fan 160, and the first fan motor 165 of the first blowing device 100, and therefore, repetitive disclosure has been omitted.

The second blowing device 200 may include a third air guide device or guide 270, which may be coupled to an upper side of the second fan 260 to guide flow of air passing through the second fan 260. The third air guide 270 may be the same or similar to the first air guide 170, and therefore, repetitive description has been omitted.

The third air guide 270 may include a guide device or guide that guides movement of the flow adjusting device 300. The guide may include a first rack and a shaft guide groove.

The second blowing device 200 may include a second discharge guide device or guide 280, which may be disposed or provided at or on an upper side of the third air guide 270 and guide the flow of air passing through the third air guide 270. The flow adjusting device 300 may be movably provided on or at an upper side of the second discharge guide 280. The flow adjusting device 300 may include a third fan 330. The third fan 330 may guide air passing through the third air guide 270 to be discharged outside of the air cleaner 10. A third fan motor 335 may be coupled to the third fan 330.

The third fan 330 may include an axial flow fan. The third fan 330 may be operated to allow air introduced in the axial direction by passing through the third air guide 270 to be discharged in the axial direction. The air passing through the third fan 330 may be discharged to the outside through the second discharge portion 305, which may be located at or on an upper side of the third fan 330.

In the air cleaner 10, a discharged blowing amount may be improved, and air may be discharged in various directions as the second discharge portion 305 along with the first discharge portion 105 of the first blowing device 100 may be provided.

The display device 600, which may display operation information of the air cleaner 10, may be provided on or at an upper surface of the air cleaner 10. The display device 600 may include a display PCB 618. The display PCB 618 may be installed or provided in a space between an upper surface of the air cleaner 10 and the third fan 330.

The first fan motor 165 and the second fan motor 265 may be disposed or provided in series relative to a longitudinal direction of the air cleaner 10. In addition, the second fan motor 265 and the third fan motor 335 may be disposed or provided in series relative to the longitudinal direction of the air cleaner 10.

The flow adjusting device 300 may further include a rotation guide device or guide, that guides rotation in the lateral direction of the flow adjusting device 300 and rotation in the vertical direction of the flow adjusting device 300. The rotation in the lateral direction may be referred to as a "first direction rotation" and the rotation in the vertical direction may be referred to as a "second direction rotation."

The rotation guide may include a first guide mechanism or guide that guides the first direction rotation of the flow adjusting device 300 and a second guide mechanism or guide that guides the second direction rotation of the flow adjusting device 300. The first guide may include a first gear motor 363 that generates a drive force, and a first gear 360 rotatably coupled to the first gear motor 363. For example, the first gear motor 363 may include a step motor, a rotation angle of which may be easily controlled.

The second guide may include a rotation guide member or guide 370 (see FIG. 16) that guides the second direction rotation of the flow adjusting device 300. The rotation guide 370 may include a rack 374.

The second guide may include a second gear motor 367 that generates a drive force, and a second gear 365 coupled to the second gear motor 367. For example, the second gear motor 367 may include a step motor. If the second gear motor 367 is driven, the rotation guide 370 may rotate in the vertical direction by linkage of the second gear 365 and the second rack 374. Accordingly, the flow adjusting device 300 may perform the second direction rotation according to the movement of the rotation guide 370.

If the flow adjusting device 300 performs the second direction rotation, the flow adjusting device 300 may be in a "second position" in which it protrude from the upper surface of the air cleaner 10 (see FIG. 16). On the other hand, as shown in FIG. 3, the position in which the flow adjusting device 300 is laid out may be referred to as a "first position."

Referring to FIG. 5, the first case 101 may form an outer appearance of the first blowing device 100, and may surround inner components of the first blowing device 100, that is, the first fan 160 and the first fan housing 150. In addition, air introduced to the inside of the first case 101 through the first suction portion 102 formed in the first case 101 may pass through the first filter 120. In particular, the first suction portion 102 may include a suction portion which is disposed at a higher position than the first filter 120. Air which is suctioned through the suction portion may flow in a space formed between the first fan housing 150 and the first case 101, and flow in the downward direction toward the first filter 120. Then, the air may flow inside of the first filter 120 through the outer circumferential surface of the first filter 120.

Similarly, the second case 201 may form an outer appearance of the second blowing device 200, and may surround inner components of the second blowing device 200, that is, the second fan 260 and the second fan housing 250. In addition, air which is introduced to the inside of the second case 201 through the second suction portion 202 formed in the second case 201 may pass through the second filter 220. In particular, the second suction portion 202 may include a suction portion which is disposed at a higher position than the second filter 220. Air which is suctioned through the suction portion may flow in a space which is formed between the second fan housing 250 and the second case 201, and flow in the downward direction toward the second filter 220. Then, the air may flow inside of the second filter 220 through the outer circumferential surface of the second filter 220.

Hereinafter, a relative position of a case and a fan housing will be described with reference to the accompanying drawings.

Figure 10:
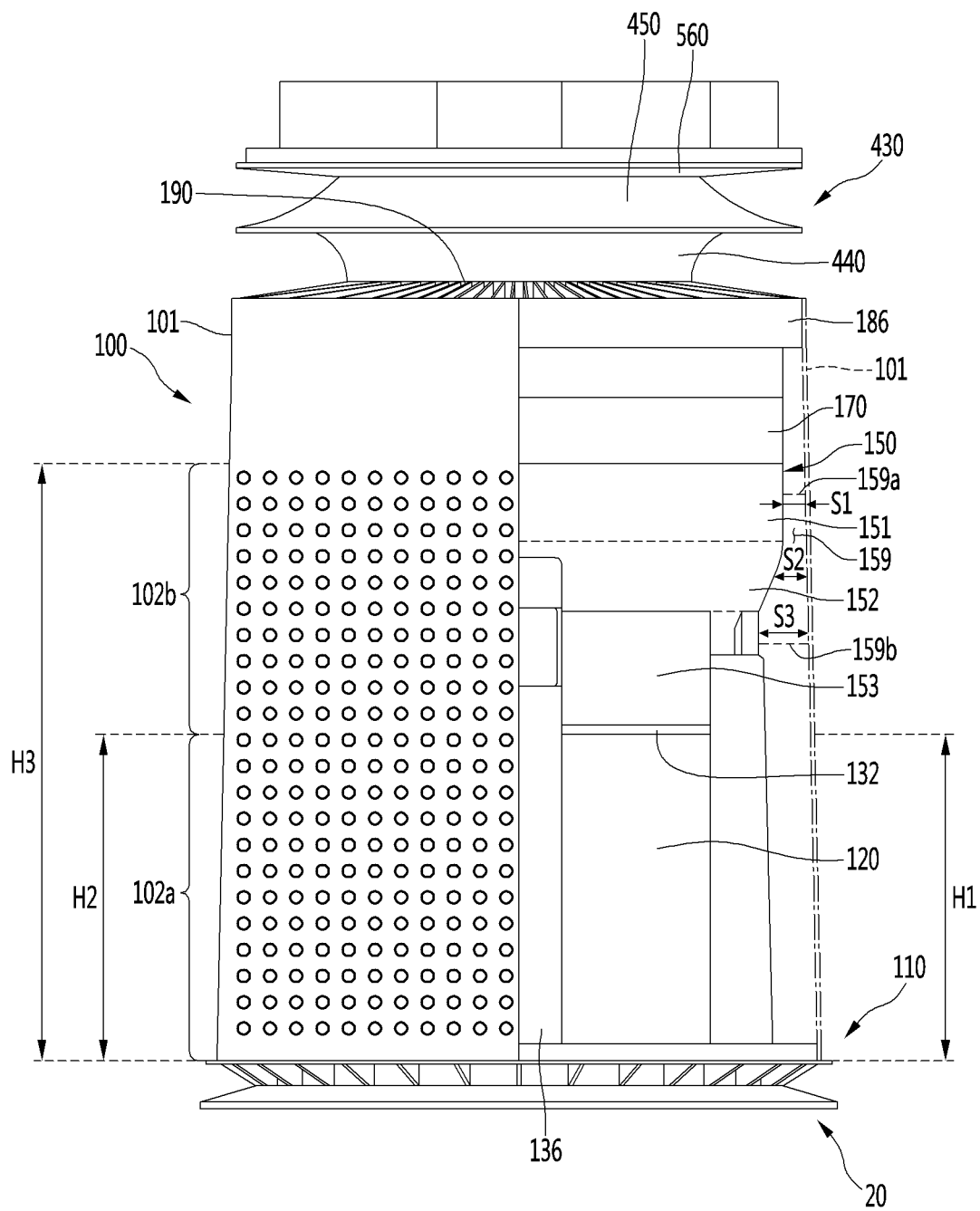
FIG. 10 is a view illustrating a coupling position of a first fan housing and the first case of the air cleaner of FIG. 1.
Figure 11:
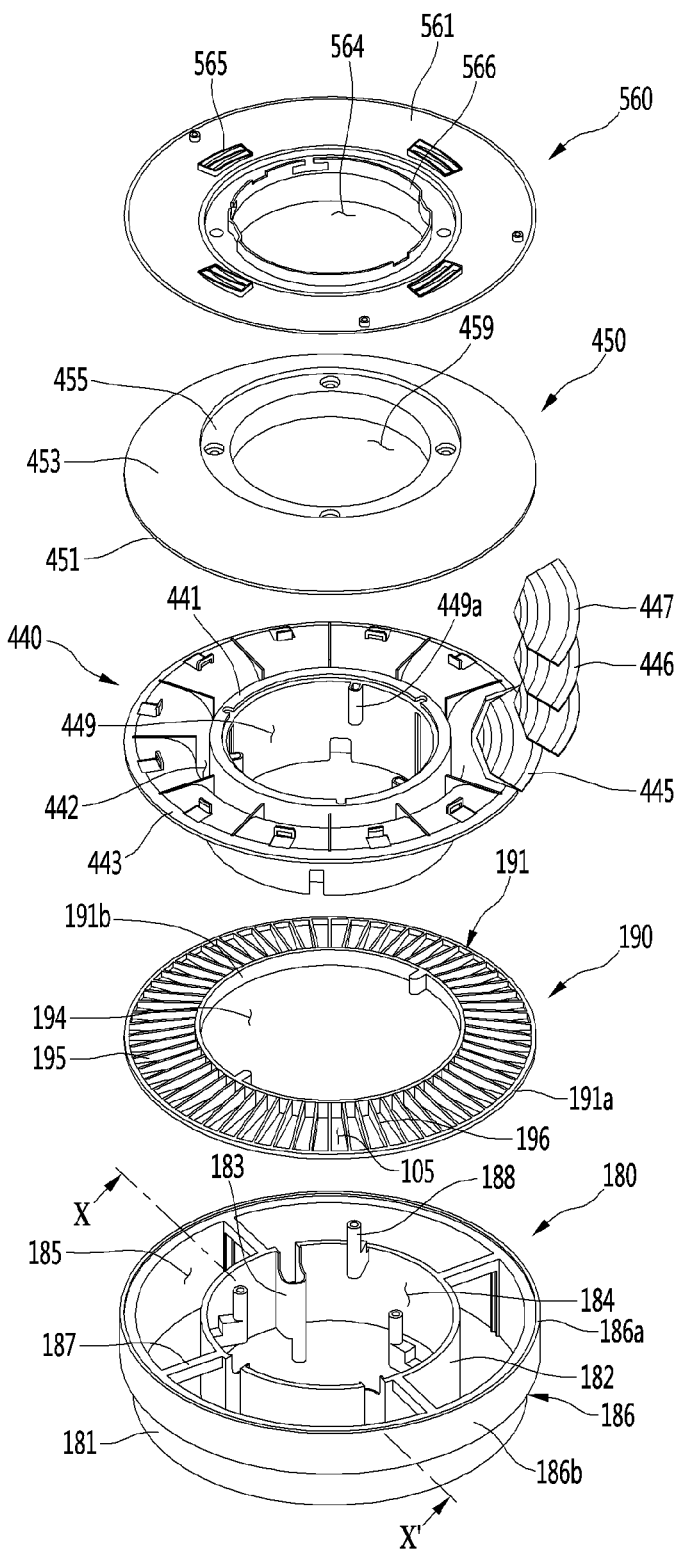
FIG. 11 is an exploded perspective view of a dividing plate and components coupled to the dividing plate according to an embodiment.
Figure 12:
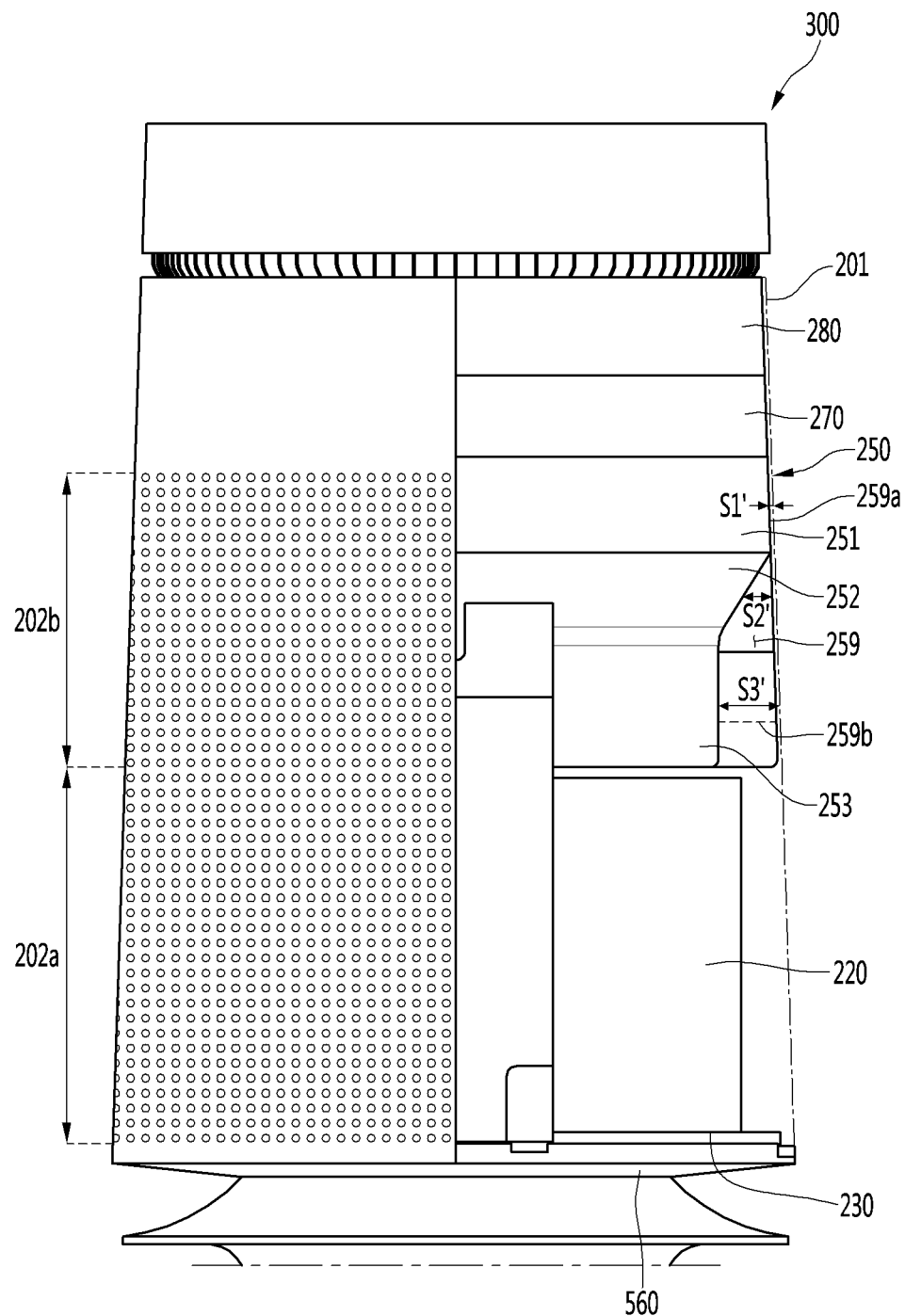
FIG. 12 is a view illustrating a coupling position of a second fan housing and a second case according to an embodiment.
Figure 13:
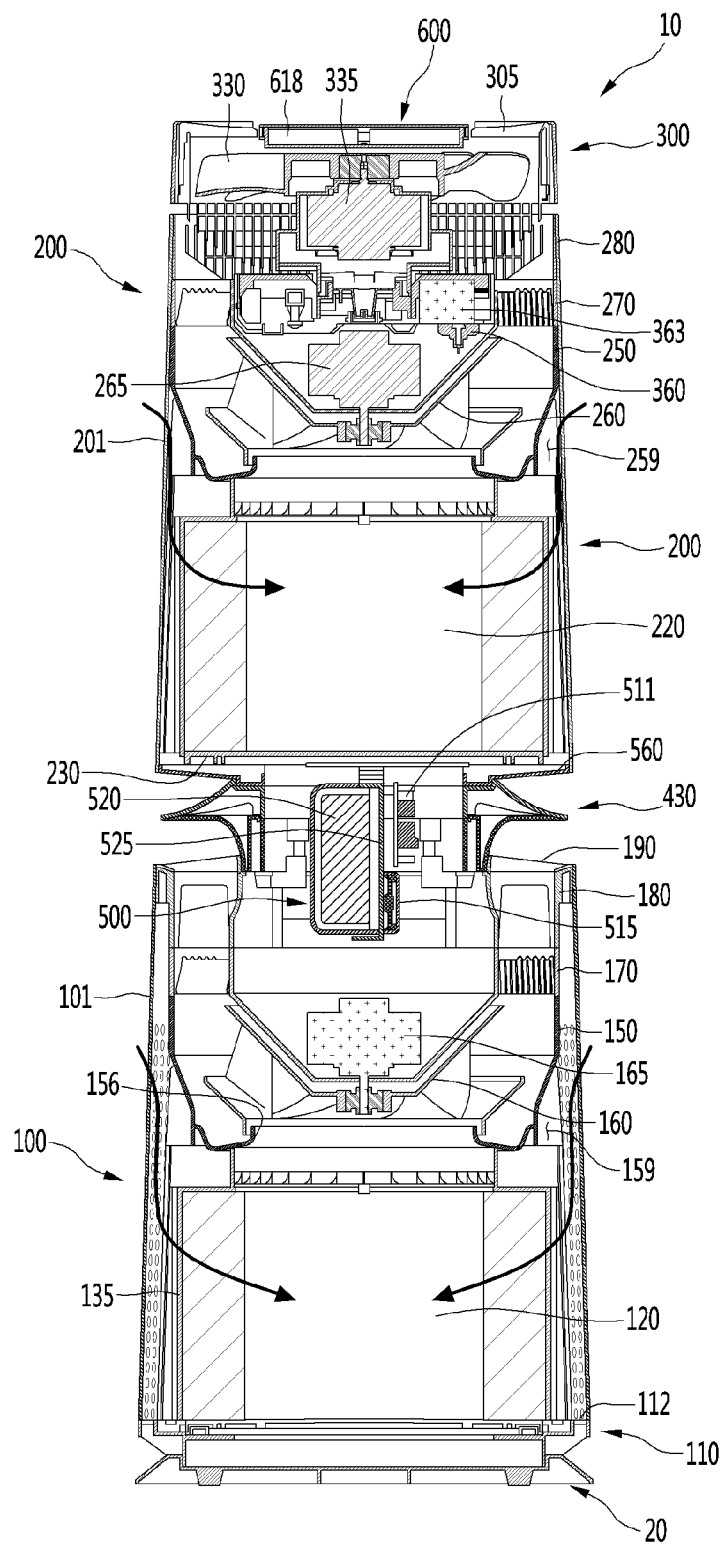
FIG. 13 is a cross-sectional view illustrating a state in which air is suctioned from an upper side of a filter to pass through the filter in the air cleaner of FIG. 1.

FIG. 10 is a view illustrating a coupling position of the first fan housing and the first case of the air cleaner of FIG. 1. FIG. 11 is an exploded perspective view of a dividing plate and components coupled to the dividing plate according to an embodiment. FIG. 12 is a view illustrating a coupling position of the second fan housing and the second case according to an embodiment. FIG. 13 is a cross-sectional view illustrating a state in which air is suctioned from the upper side of a filter to pass through the filter in the air cleaner according to FIG. 1.

First, referring to FIGS. 10, 11 and 4, the first blowing device 100 according to this embodiment may further include a second air guide device or guide 180, which may be coupled to the upper side of the first air guide 170 and guide air having passed through the first air guide 170 to the discharge guide 190. The second air guide 180 may include a first guide wall 181, which may have a substantially cylindrical shape, and a second guide wall 182, which may be positioned at an inside of the first guide wall 181 and have a substantially cylindrical shape. The first guide wall 181 may be disposed or provided to surround the second guide wall 182.

A second air flow path 185, through which air may flow, may be formed between an inner circumferential surface of the first guide wall 181 and an outer circumferential surface of the second guide wall 182. Air which flows along the first air flow path 172a of the first air guide 170 may flow in the upward direction through the second air flow path 185. The second air flow path 185 may be referred to as a "discharge flow path." In addition, the first discharge portion 105 may be provided on or at an upper side of the second air flow path 185.

A fastening guide 183, which may be coupled with the first air guide 170, may be provided on a lower portion of the second guide wall 182. The fastening guide 183 may extend to the lower side of the second guide wall 182.

A predetermined fastening member may be coupled to the fastening guide 183, and the fastening member may be coupled to a fastening rib 178 of the first air guide 170. The fastening rib 178 may project from an upper surface of the motor accommodating portion 173 in the upward direction. In addition, a plurality of fastening guides 183 may be provided. The plurality of fastening guides 183 may be spaced apart from one another in the circumferential direction. For example, three fastening guides 183 and three fastening ribs 178 may be provided.

The second air guide 180 may further include a wall supporting portion or support 187 that extends from an inner circumferential surface of the first guide wall 181 to an outer circumferential surface of the second guide wall 182. By the wall supporting portion 187, the first and second guide walls 181 and 182 may be stably coupled to each other. A plurality of wall supporting portions 187 may be provided. For example, the plurality of wall supporting portions 187 may include four wall supporting portions 187 extending in four directions. In addition, the first discharge guide 190 may be supported on the plurality of wall support portions 187.

A first space portion 184, in which at least a portion of a printed circuit board (PCB) device 500 may be accommodated, may be formed inside of the second guide wall 182 and have a cylindrical shape. The PCB device 500 may include a power supply portion or power supply 520 and a main PCB 511.

The power supply portion 520 may refer to a device that receives commercial power supplied from a power line connected to the air cleaner 10 to supply power to the main PCB 511 and a plurality of components in the air cleaner 10. The power supply 520 may include a PCB (power PCB) for AC power. The main PCB 511 may include a PCB for DC power, which may be driven by a DC voltage converted in the PCB for AC power.

The PCB device 500 may further include a PCB supporting plate 525 that supports the power supply portion 520 and the main PCB 511. The main PCB 511 may be supported on one or a first surface of the PCB supporting plate 525, and the power supply portion 520 may be supported on the other or a second surface of the PCB supporting plate 525.

The PCB device 500 may include a communication module 515 through which the air cleaner 10 is capable of communicating with an external device. For example, the communication module 515 may include a Wi-Fi module. The communication module 515 may be supported on the PCB supporting plate 525, and may be disposed or provided at a lower side of the main PCB 511.

The second air guide device 180 may further include a second coupling portion 188, which may be provided on the inner circumferential surface of the second guide wall 182 to be coupled to the dividing plate 430. The dividing plate 430 may include a first coupling portion 449*a*, which may be coupled to the second coupling portion 188.

A plurality of second coupling portions 188 may be provided. The plurality of second coupling portions 188 may be spaced apart from one another to be arranged in the circumferential direction. For example, three second coupling portions 188 and three first coupling portions 449*a* may be provided.

The second air guide device 180 may include a bending portion 186 which may be bent in an outside direction from an outer circumferential surface of the second air guide 180.

The bending portion 186 may extend in the outside direction from an upper portion of the first guide wall 181. The bending portion 186 may form an edge portion or edge of the second air guide 180, and may form an outermost portion of the second air guide 180.

The bending portion 186 may extend to the outside in the radial direction from an upper end of the first guide wall 181 and be bent in the downward direction. For example, the bending portion 186 may have a substantially "┐" or eave shape. The bending portion 186 may include a first extending portion that extends to the outside in the radial direction from the first guide wall 181 and a second extending portion that extends in the downward direction from the first extending portion. The first extending portion may be a portion that supports the edge portion or edge of the first discharge guide 190, and the second extending portion may be a portion that supports an inner surface of the first case 101.

The first blowing device 100 may include a first discharge guide device or guide 190, which may be disposed or provided on or at an upper side of the second air guide 180, that is, an outlet side of air flow passing through the second air guide 180 and guide the air outside of the air cleaner 10. That is, the second air guide 180 may be disposed or provided at a suction side of the first discharge guide 190.

The first discharge guide 190 may include a first may discharge main body 191, which may form the second space portion 194 at a substantially central portion thereof. The first discharge main body 191, may include a main body outer wall 191*a* that forms an outer circumferential surface thereof and a main body inner wall 191*b* that forms an inner circumferential surface thereof. The main body outer wall 191*a* may surround the main body inner wall 191*b*. By the configuration of the main body outer wall 191*a* and the main body inner wall 191*b*, the first discharge main body 191 may have an annular shape.

The second space portion 194 may be formed inside of the main body inner wall 191*b*. At least a portion of the PCB device 500 may be accommodated in the second space portion 194. The second space portion 194 may be formed on or at an upper side of the first space portion 184, and the first space portion 184 and the second space portion 194 may form an installation space portion or space in which the PCB device 500 may be installed or provided.

The first discharge main body 191 may include a first discharge grill 195. The first discharge grill 195 may extend to the outside in the radial direction toward the main body outer wall 191*a* from the main body inner wall 191*b*. A plurality of first discharge grills 195 may be provided, and first discharge portions or outlets 105, through which air may discharged to the outside, may be formed between the plurality of first discharge grills 195. The plurality of first discharge grills 195 may be disposed or provided on or at an upper side of the second air flow path 185, and air passing through the second air flow path 185 may be discharged through the first discharge portion 105 while flowing toward the first discharge grill 195. An air flow path formed from the second air flow path 185 to the first discharge portion 105 may be referred to as a "discharge flow path."

The second blowing device 200 may include a supporting device or support that supports a lower portion of the second filter 220 and a lever device or lever which may be provided on or at a lower side of the supporting device. The supporting device and the lever device may have the same or a similar configuration as the supporting device 140 and the lever device 142 of the first blowing device 100, and therefore, repetitive disclosure has been omitted.

The second blowing device 200 further may include a lever supporting device or support 560 that supports the second filter 220 or the lever device of the second blowing device 200. The lever supporting device 560 may have a substantially annular shape. The lever supporting device 560 may include a third space portion or space 564 that defines an installation space in which the PCB device 500 may be located or provided. The third space portion 564 may be formed at a substantially center portion of the lever supporting device 560 by passing through the lever supporting device 560 in the vertical direction.

The lever supporting device 560 may include a lever supporting main body 561, which may have an annular shape. The lever supporting main body 561 may extend toward an outer circumferential surface from an inner circumferential surface thereof to be slightly inclined in the upward direction relative to the axial direction. That is, the surface forming the lever supporting main body 561 may form an inclined surface. A space between the inclined surface and the upper surface of the dividing plate 430 may provide a space portion or space, in which a user's hand may be located.

The lever supporting main body 561 may be referred to as a "blocking portion" in that air which is discharged through the first discharge portion 105 of the first blowing device 100 may be blocked from being introduced to the second blowing device 200. The lever supporting device 560 may further include a movement guide portion or guide 565 that protrudes from the lever supporting main body 561 in the upward direction. The movement guide 565 may have the same or a similar configuration as the movement guide 113 of the first blowing device 100, and therefore, repetitive disclosure has been omitted. For convenience of description, the movement guide 113 may be referred to as a "first movement guide portion or guide," and the movement guide 565 may be referred to as a "second movement guide portion or guide."

The lever supporting device 560 may further includes a supporting projection 566 that protrudes from an inner circumferential surface of the lever support main body 561 in the upward direction. The supporting projection 566 may support the lever device of the second blowing device 200.

The dividing device 400 may be provided between the first blowing device 100 and the second blowing device 200. The dividing device 400 may include the dividing plate 430 that separates or blocks air flow generated in the first blowing device 100 and air flow generated in the second blowing device 200. By the dividing plate 430, the first and second blowing devices 100 and 200 may be spaced apart from each other in the vertical direction.

That is, a separation space in which the dividing plate 430 is located may be formed between the first and second blowing devices 100 and 200. The first discharge guide 190 of the first blowing device 100 may be located at a lower end portion or end of the separation space, and the lever supporting device 560 of the second blowing device 200 may be located at an upper end portion or end of the separation space.

The separation space may be divided into an upper space and a lower space by the dividing plate 430. The lower space may be a first space portion or space, through which air discharged from the first discharge portion 105 of the first discharge guide 190 may pass in a process in which the air flows to the outside of the air cleaner 10. In addition, the upper space may be a grasping space in which a user may put his or her a hand when moving the air cleaner 10.

Air discharged from the first discharge portion 105 may be guided by the dividing plate 430 to flow to the outside of the air cleaner 10. Accordingly, it is possible to prevent the air from being introduced into the second blowing device 200.

The dividing plate 430 may include a first plate 440, and a second plate 450 coupled to the first plate 440. The second plate 450 may be provided on or at an upper side of the first plate 440. In addition, the first plate 440 may extend rounded in the upward direction, and the second plate 450 may extend rounded in the downward direction.

The first plate 440 may include a plate inner wall 441, which may have a substantially annular shape, and a plate outer wall 443, which may surround the plate inner wall 441. A first space portion or space 449 that passes through the first plate 440 in the vertical direction may be formed at a center portion of the plate inner wall 441. The first space portion 449 may provide an installation space in which at least a portion of the PCB device 500 may be located or provided.

The plate outer wall 443 may extend to the outside in the radial direction from the plate inner wall 441. The first plate 440 may further include a depression portion or description 442 which defines a space between the plate inner wall 441 and the plate outer wall 443. The depression portion 442 may be depressed in the downward direction from a space between the upper end portion of the plate inner wall 441 and the upper end portion of the plate outer wall 443.

The first plate 440 may include a first coupling portion 449a, which may be coupled to the second air guide 180. The first coupling portion 449a may be provided on an inner circumferential surface of the plate inner wall 441. In addition, the first coupling portion 449a may be coupled to a second coupling portion 188 of the second air guide 180. The second coupling portion 188 may be provided on an inner circumferential surface of the second guide wall 182.

A display device or display 460 that displays information relative to an operation of the air cleaner 10 may be installed or provided at the dividing plate 430. For example, the information may include information on an air pollution level or air cleanliness.

The display device 460 may be installed or provided in a space between the first plate 440 and the second plate 450. A device mounting portion or mount 445, on which the display device 450 may be mounted, may be formed on the first plate 440. The device mounting portion 445 may be formed on an upper surface of the plate outer wall 443.

The display device 460 may include an illumination source 462. The illumination source 462 may be installed or provided at an illumination supporting portion or support 461. The illumination supporting portion 461 may include a mounting groove into which the illumination source 462 may be inserted. For example, the illumination source 462 may include a light emitting diode (LED).

The display device 460 may include a reflecting plate 447, which may be provided on or at at least one side of the diffusing portion 446 and reflect light diffused through the diffusing portion 446 so as to concentrate the light on an outer circumferential surface of the dividing plate 430. For example, the reflecting plate 447 may be provided on each of upper and lower sides of the diffusing portion 446. According to this configuration, light irradiated from the illumination source 462 may be concentrated on the diffusing portion 446 by the reflecting plate 447, and is capable of being converted into diffused light while passing through the diffusing portion 446.

The second plate 450 may include a second plate main body 451, which may have a substantially annular shape. The second plate 450 may include a plate mounting portion or mount 455, which may protrude to the inside in the radial direction from an inner circumferential surface of the second plate main body 451. The plate mounting portion 455 may be depressed in the downward direction from an upper end portion or end of the second plate main body 451, and support the lever supporting device 210.

A fifth space portion or space 459, which may pass through the plate mounting portion 455 in the vertical direction, may be formed at a center portion of the plate mounting portion 455. The fifth space portion 459 may provide an installation space in which at least a portion of the PCB device 500 may be located or provided. The fifth space portion 459 may be aligned on or at a lower side of a fourth space portion or space 564. The first to fifth space portions 184, 194, 564, 449, and 459 may be aligned in the vertical direction, to provide an installation space for the PCB device 500.

The second plate main body 451 may extend at an incline toward the outside in the radial direction. The second plate main body 451 may include an inclined surface 453 that extends at an incline in the downward direction toward an outer circumferential surface from an inner circumferential surface of the second plate main body 451. For example, the inclined surface 453 may have a surface that extends rounded.

The first case 101 may be supported by the suction grill 110 to extend in the upward direction. For example, the first case 101 may be supported on the upper surface or outer circumferential surface of the suction grill 110 to extend in the upward direction.

In addition, the first case 101 may surround inner components of the first blowing device 100, that is, the first filter 120, the first filter frame 130, the first fan housing 150, the first air guide 170, and the second air guide 180. That is, the inner components of the first blowing device 100 may be accommodated inside of the first case 101.

An inner circumferential surface of the upper portion of the first case 101 may be supported by the second extending portion of the bending portion 186. For example, an outer surface of the second extending portion of the bending portion 186 may be coupled to the inner circumferential surface of the upper portion of the first case 101.

An outer surface of the first fan housing 150, an outer surface of the first air guide 170, and an outer surface of the first guide wall 181 of the second air guide 180 may be spaced apart from one another in the inside direction from the inner surface of the first case 101. This results from a configuration in which the bending portion 186 of the second air guide 180 further protrudes to the outside in the radial direction than the first fan housing 150 and the first air guide 170.

A plurality of first suction portions 102, which may be provided on or at an outer circumferential surface of the first case 101 may be formed from a lower portion of the first case 101 to an upper portion of the first case 101. For example, the first suction portion 102 may be formed to a height at which the first fan housing 150 is located.

The first suction portion 102 may include a plurality of lower suction portions or inlets 102a, which may be formed from a lower portion of the first case 101 to a height at which the first filter 120 is located, and a plurality of upper suction portions or inlets 102b, which may be formed from an upper side of the plurality of lower suction portions 102a to an upper portion of the first case 101.

The plurality of lower suction portions 102a may be disposed or provided at heights corresponding to the first filter 120. In addition, the plurality of upper suction portions 102b may be disposed or provided at higher positions than the first filter 120.

In summary, when the height of the suction grill 110 is defined as a reference point, the first filter 120 may extend in the upward direction from the suction grill 110, and the upper end portion of the first filter 120 may be located at a first height H1. In addition, the plurality of lower suction portions 102a may be formed to a second height H2 from the suction grill 110. That is, uppermost suction portions among the plurality of lower suction portions 102a may be formed at the second height H2. The first height H1 and the second height H2 may have a same value.

The plurality of upper suction portions 102b may be disposed on the upper side of the first filter 120, and may be formed to a third height H3 from the suction grill 110. That is, uppermost suction portions among the plurality of upper suction portions 102b may be formed at the third height H3. It will be apparent that the third height H3 may have a greater value than the first height H1 and the second height H2.

An outer surface of the first fan housing 150 and an inner surface of the first case 101 may be spaced apart from each other. A housing suction flow path 159, through which air suctioned through the upper suction portion 102b may flow in the first filter 120 may be formed in a space between the outer surface of the first fan housing 150 and the inner surface of the first case 101. The housing suction flow path 159 may communicate with the upper suction portion 102a.

The housing suction flow path 159 may include a first inlet portion or inlet 159a, which may be formed in a space between an outer surface of the first main body 151 and the inner surface of the first case 101, and a second inlet portion or inlet 159b, which may be formed in a space between an outer surface of the third main body 153 and the inner surface of the first case 101. Air which is suctioned through the upper suction portion 102b may be introduced to the housing suction flow path 159 through the first inlet portion 159a, and air which passes through the first inlet portion 159a may be discharged from the housing suction flow path 159 through the second inlet portion 159b. The discharged air may flow inside of the first filter 120.

As described above, a first set or predetermined diameter of the first main body 151 may be greater than a second set or predetermined diameter of the third main body 153. Therefore, a distance from the outer surface of the first main body 151 to the inner surface of the first case 101, that is, a first width S1 in the radial direction of the first inlet portion 159a may be formed smaller than a distance from the outer surface of the third main body 153 to the inner surface of the first case 101, that is, a second width S2 in the radial direction of the second inlet portion 159b.

In addition, the second main body 152 may extend in the downward direction toward an upper end portion or end of the third main body 153 from a lower end portion or end of the first main body 151, and may be configured such that a diameter of the second main body 152 gradually decreases. Therefore, the distance S2 from the outer surface of the second main body 152 to the inner surface of the first case 101 may gradually increase in the downward direction. In addition, the distance S2 may be equal to or greater than the distance S1, and may be equal to or smaller than a distance S3. That is, the width of the housing suction flow path 159 may increase in an air flow direction.

According to this configuration, a size of a flow path of air which is suctioned through the upper suction portion 102b and flows in the housing suction flow path 159 may gradually increase toward the first filter 120. Thus, a flow performance of air which flows in the housing suction flow path 159 through the upper suction portion 102b may be improved, and a suction amount of air may be increased.

The second blowing device 200 may include a second case 201, which may surround the plurality of components. The second case 201 may be supported by the lever supporting device 560 to extend in the upward direction. For example, an inner circumferential surface of a lower portion of the second case 201 may be supported on an outer circumferential surface of the lever supporting device 560.

The second case 201 may include a plurality of second suction portions 202. The second suction portions 202 may include a lower suction portion 202a, which may be disposed or provided at a height corresponding to the second filter 220 and an upper suction portion 202b, which may be disposed or provided on or at an upper side of the second filter 220.

The second fan housing 250 may include a first main body 251, a second main body 252, and a third main body 253, which may have diameters different from one another. The first main body 251 may have a third set or predetermined diameter, and the second main body 252 may extend at an incline such that its diameter decreases toward a lower side of the first main body 251. The third main body 253 may extend from a lower side of the second main body 252 and may have a fourth set or predetermined diameter. This configuration is similar to the configuration of the first fan housing 150, and therefore, repetitive disclosure has been omitted.

An outer surface of the second fan housing 250 and an inner surface of the second case 210 may be spaced apart from each other at a predetermined distance, and a housing suction flow path 259 may be formed in the space. The housing suction flow path 259 may include a first inlet portion or inlet 259a, which may be formed in a space between an outer surface of the first main body 251 and the inner surface of the second case 201, and a second inlet portion or inlet 259b, which may be formed in a space between an outer surface of the third main body 253 and the inner surface of the second case 201.

A first width S1' of the first inlet portion 259a may be smaller than a second width S3' of the second inlet portion 259b. In addition, a distance S2' from the outer surface of the second main body 259 to the inner surface of the second case 201 may be equal to or greater than the width S1', and may be equal to or smaller than the width S3'.

Air which is suctioned inside of the second case 210 from the upper suction portion 202b may be introduced to the housing suction flow path 259 through the first inlet portion 259a, and discharged from the housing suction flow path 259 through the second inlet portion 259b. Then, the discharged air may flow inside of the second filter 220.

According to this configuration, a size of a flow path of air which is suctioned through the upper suction portion 202b and flows in the housing suction flow path 259 may gradually increase toward the second filter 220. Thus, a flow performance of air which flows in the housing suction flow path 259 through the upper suction portion 202b may be improved, and a suction amount of air may be increased.

Meanwhile, the size of the housing suction flow path 269 of the second blowing device 200 may be smaller than the size of the housing suction flow path 159 of the first blowing device 100. This is because, while the size of the first case 101 may be greater than the size of the second case 201, the sizes of the first fan housing 150 and the second fan housing 250 may be equal to each other. In addition, this is because while the first case 101 is relatively spaced apart from the second fan housing 250 by being supported on the bending portion 186 of the second air guide 180 and extending in the downward direction, the second case 210 may be disposed or provided relatively adjacent to the second fan housing 250.

The flow of air which is suctioned through each of the upper suction portions 102b and 202b of the first and second cases 101 and 201 will be briefly described with reference to FIG. 13.

As described above, the first suction portion 102 of the first case 101 may include the upper suction portion 102b which may be located on or at the upper side of the first filter 120. If the first fan 160 is driven, at least a portion of air in an indoor space may be suctioned inside of the first case 101 through the upper suction portion 102b.

The suctioned air may flow in the downward direction along the outer surface of the first fan housing 150. Air may flow in the second inlet portion 159b via the first inlet portion 159a of the housing suction flow path 159. Air which is discharged from the second inlet portion 159b may flow through the outer circumferential surface of the first filter 120, and foreign materials may be filtered in a process of introduction of the air to the inside of the first filter 120. Then, air which passes through the first filter 120 may flow in the upward direction and be introduced inside of the first fan housing 150.

The second suction portion 202 of the second case 201 may include the upper suction portion 202b, which may be located on or at an upper side of the second filter 220. If the second fan 260 is driven, at least a portion of air in an indoor space may be suctioned to the inside portion of the second case 201 through the upper suction portion 202b.

The suctioned air may flow in the downward direction along the outer surface of the second fan housing 250. Air may flow in the second inlet portion 259b via the first inlet portion 259a. Air which is discharged from the second inlet portion 259b may flow through the outer circumferential surface of the second filter 220, and foreign materials may be filtered in a process of introduction of the air to the inside of the second filter 220. Then, air which passes through the second filter 220 may flow in the upward direction and be introduced to the inside portion of the second fan housing 250.

Figure 14:
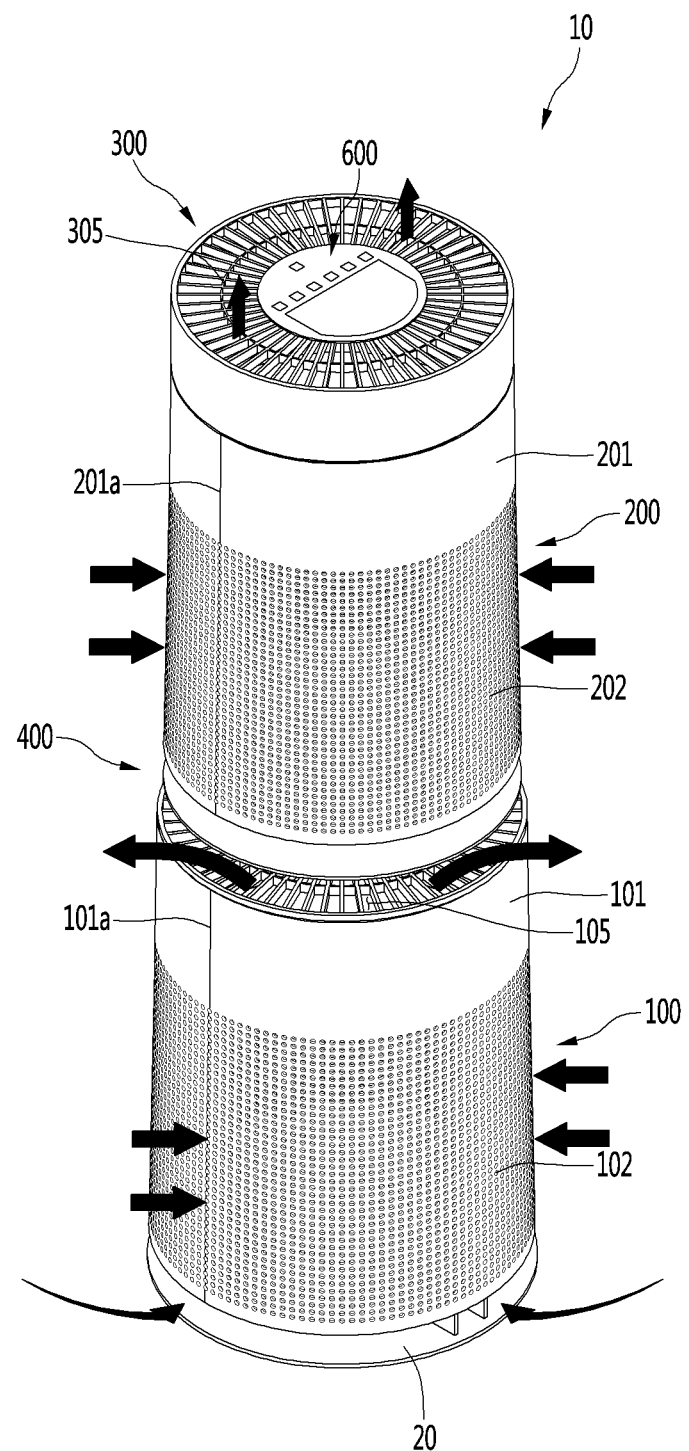
FIGS. 14 to 16 are views illustrating an air flow state in the air cleaner of FIG. 1.
Figure 15:
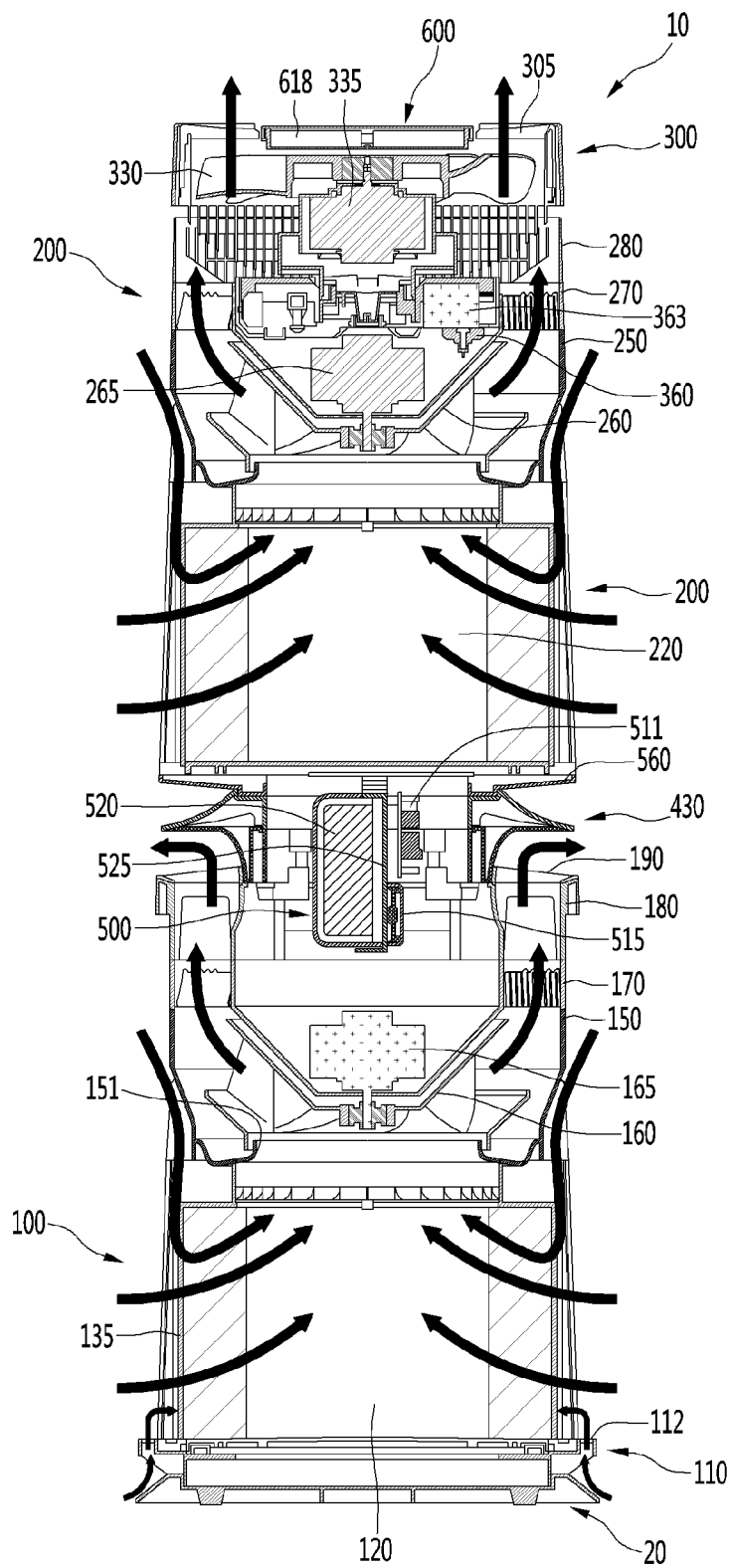

FIGS. 14 to 16 are views illustrating a state in which air flows in the air cleaner of FIG. 1.

First, a flow of air according to operation of the first blowing device 100 is described hereinafter. When the first fan 160 is driven, indoor air is suctioned into the inside of the first case 101 through the first suction portion 102 and the base suction portion 103. The suctioned air passes through the first filter 120 and foreign materials in the air may be filtered in this process. In the process of the air passing through the first filter 120, air may be suctioned in a radial direction of the first filter 120, filtered, and then flow in the upward direction.

Air which is sucked through the lower suction portion 102a of the first suction portion 102 may pass through the first filter 120 while flowing toward the inside in the radial direction. In addition, air which is sucked through the upper suction portion 102b may flows in the downward direction along the housing suction flow path 159, flow toward the outer circumferential surface of the first filter 120, and then pass through the first filter 120. Air which is suctioned through the base suction portion 103 may flow toward the outer circumferential surface of the first filter 120 and then pass through the first filter 120. In the process in which air which is suctioned through the first suction portion 102 and the base suction portion 103 passes through the first filter 120, the air is suctioned in the radial direction of the first filter 120, is filtered, and then flows in the upward direction.

The air which is passed through the first filter 120 may flow to the upper side in the radial direction while passing through the first fan 160 and stably flow in the upward direction while passing through the first air guide 170 and the second air guide 180. Air passing through the first air guide 170 and the second air guide 180 may pass by the first discharge guide 190 and flow in the upward direction through the first discharge portion 105.

Air which is discharged through the first discharge portion 105 may be guided by the dividing plate 430, which may be positioned at the upper side of the first discharge guide 190, and thus, may be discharged to the outside of the air cleaner 10. In particular, the direction in which air may flow in the upward direction may be changed while the air is flowing along the curved surface portion 444a and the flat surface portion 444b, which are provided on the first plate 440 of the dividing plate 430.

As the outermost portion in the radial direction of the dividing plate 430 is located outward of the outermost portion of the flow path of air discharged through the first discharge portion 105, it is possible to prevent the air discharged from the first discharge portion 105 from flowing in the upward direction, and the discharging of air in the radial direction may be effectively guided.

When the second fan 260 is driven, indoor air may be suctioned into the inside of the second case 201 through the second suction portion 202, The suctioned air may pass through the second filter 220, and in this process, foreign materials in the air may be filtered. In the process of the air passing through the second filter 220, air may be suctioned in the radial direction of the first filter 120, filtered, and then flow in the upward direction.

Air which is suctioned through the lower suction portion 202a of the second suction portion 202 may pass through the second filter 220 while flowing toward the inside in the radial direction. In addition, air which is suctioned through the upper suction portion 202b may flow in the downward direction along the housing suction flow path 259, flow toward the outer circumferential surface of the second filter 220, and then pass through the second filter 220. In the process in which air passes through the second filter 220, the air may be suctioned in the radial direction of the second filter 220, filtered, and then flow in the upward direction.

Air which passes through the second filter 220 may flow to the upper side in the radial direction while passing through the second fan 160, and stably flow in the upward direction while passing through the third air guide 270 and the second discharge guide 280. Air which passes through the third air guide 270 and the second discharge guide 280 may be discharged through the second discharge portion 305 via the flow adjusting device 300.

At this time, if the flow adjusting device 300 is in the first position in which the flow adjusting 300 is laid out, as shown in FIGS. 14 and 15, air which is discharged from the flow adjusting device 300 may flow in the upward direction. On the other hand, if the flow adjusting device 300 is in the second position in which the flowing adjusting device 300 is inclined, as shown in FIG. 16, air which is discharged from the flow adjusting device 300 may flow toward the front upper side. By the flow adjusting device 300, an amount of air which is discharged from the air cleaner 10 may be increased, and purified air may be supplied up to a position a far distant from the air cleaner 10.

According to, a suction capacity may be improved as the suction portion may be formed along an outer circumferential surface of a cylindrical case and a structural resistance of the case may not be generated in an air suction process. In particular, a plurality of apertures may be included on the suction portion and a suction flow path which may be directed to the inside portion of the air cleaner may be formed in 360 degree directions relative to the air cleaner, as the plurality of apertures may be formed evenly over an entire outer circumferential surface of the case. Finally, a suction area of air may be increased and air around a person in a room may be sufficiently suctioned where the person in the room sitting down or standing up.

In addition, as some suction portions among the suction portions are formed at a height corresponding to a filter or a position lower than the filter, air may be suctioned to the filter through the some suction portions. As the other suction portion may be formed at a position higher than the filter, the air may be sucked to the filter through the other suction portion.

Accordingly, in addition to air in an indoor space, which is located at a height corresponding to the filter, air which is located at a height lower than the filter or air which is located at a height higher than the filter may pass through the filter. The air which passes through the filter may easily move to a fan which is located on or at an upper side of the filter. Finally, a suction amount of air may be improved.

In particular, air which is located at a height higher than the filter may flow in the downward direction from the upper portion of a fan housing. As an external diameter of the fan housing in which the fan is accommodated may gradually decrease in the downward direction, an air flow path between the case and the fan housing may gradually increase. Finally, air which passes through the air flow path may be easily suctioned.

Further, as the first case or the second case may have a cylindrical shape or a cone shape (truncated cone shape), inside components of the air cleaner may be stably accommodated, and spatial utilization of the air cleaner may be improved. Furthermore, the first case or the second case may be stably supported by a filter frame, and the suction portion which may be formed in each of the first and second cases may be located relatively adjacent to the filter. Finally, a flow loss of air which flows into the filter through the suction portion may be reduced.

Two parts of the first case or the second case may be detachably coupled to each other. In particular, one or a first side portion or side of each of the two parts may be fixed by a fastening member, and a coupling state of the other or a second side portion of each of the two parts may be maintained by a magnet member or magnet. When a user accesses inside components by separating a case, an inside portion of the case may be opened by separating the magnet member, so that separation of the case may be easily performed.

Discharge of air in the upward direction may be guided through the second blowing device and discharge of air in the frontward direction may be guided by the flow adjusting device, which may be provided on or at an upper side of the second blowing device. Discharge of air in a lateral direction may be guided, in a process of rotating of the flow adjusting device. Finally, an air cleaning function of the indoor space may be improved as discharge of air in various directions may be guided relative to the air cleaner and a discharge air flow may extend a long distance from the air cleaner. A air flow may be easily generated toward a circumferential space of the person in the room whether the person in the room sitting down or standing up.

The second blowing device may be disposed or provided on or at an upper side of the first blowing device, a dividing plate may be provided between the first and second blowing devices, and air which may be discharged from the first blowing device may be guided outside in a radial direction by the dividing plate. Accordingly, it is possible to prevent a phenomenon that air which is discharged from the first blowing device is re-introduced to the second blowing device.

A discharging flow path which passes through the first discharge guide of the first blowing device may extend in the upward direction, and the dividing plate may extend sufficiently long to the outside in the radial direction from the upper side of the discharge flow path. Accordingly, it is possible to prevent air in the discharge flow path from being introduced to the second blowing device by passing through the dividing plate.

A blowing capacity of the air cleaner may be improved as a plurality of blowing devices may be provided.

The air which flows in the radial direction through a centrifugal fan may be easily guided toward the discharge portion in the upward direction, as the centrifugal fan for increasing a blowing capacity of the air cleaner and the air guide which may be disposed on or at an outlet side of the centrifugal fan may be provided.

A phenomena that interference between air flows may be prevented as the air flows which are independent from each other may be generated through the first blowing device and the second blowing device. Accordingly, an air flowing capacity may be improved.

In addition, a suction area may be increased as air may be introduced to the inside portion of the filter from all directions outside of the filter by the filter being provided in a cylindrical shape. Accordingly, as air cleaning capacity of the filter may be improved.

Embodiments disclosed herein provide an air cleaner which is capable of improving a suction capacity of air which is suctioned to the air cleaner. Embodiments disclosed herein provide an air cleaner which is capable of sufficiently suctioning air around a person in a room whether the person in the room sitting down or standing up by including a suction flow path which is directed from a circumferential direction of the air cleaner to an inside portion thereof and a suction flow path through which air may be introduced through an upper portion and a lower portion of the air cleaner.

Embodiments disclosed herein provide an air cleaner which is capable of increasing an amount of air which is suctioned through a suction portion or inlet by improving a position of the suction portion, which may be formed in a case. Embodiments disclosed herein provide an air cleaner which enables air which is suctioned through the suction portion to easily flow into a filter member or filter by improving a shape of a fan housing in which a fan of the air cleaner may be accommodated. In particular, embodiments disclosed herein provide an air cleaner which enables flow of air toward the filter to be smoothly made by improving the shape of the fan housing such that a size of the flow path of air toward the filter from the suction portion.

Embodiments disclosed herein provide an air cleaner which enables separation of a case to be easily performed and enables inside components of the air cleaner to be easily accessed by improving a structure of the case. Embodiments disclosed herein provide an air cleaner capable of discharging air from the air cleaner in various directions and sending the discharged air a long distance. In particular, embodiments disclosed herein provide an air cleaner capable of easily discharging air toward a surrounding space of a person in a room whether the person in the room sitting down or standing up by a discharge air flow being easily generated in an upward direction, a frontward direction and lateral directions of the air cleaner.

Embodiments disclosed herein provide an air cleaner capable of easily guiding air which is discharged from the air cleaner outside of the air cleaner and preventing the discharged air from being re-introduced to the air cleaner. Embodiments also disclosed herein provide an air cleaner a blowing capacity of which may be increased.

Embodiments disclosed herein provide an air cleaner in which an air guide device or guide is provided which allows air passing through a centrifugal fan to easily flow toward a discharge portion or outlet in an upward direction in a case of adopting a centrifugal fan in order to increase a blowing capacity.

Embodiments disclosed herein provide an air cleaner which improves a purification capacity of a filter and in which replacement of the filter may be easily performed. Embodiments disclosed herein provide an air cleaner in which a filter may be easily installed without an installation space for installing the filter in an inside portion of the air cleaner being additionally provided.

Embodiments disclosed herein provide an air cleaner that may include a case including a suction portion or inlet, the case having a cylindrical shape or a cone shape; a fan housing installed or provided in an inside portion of the case, the fan housing accommodating a fan therein; a filter member or filter installed or provided at a suction side of the fan, and the filter member filtering foreign materials in air which is suctioned through the suction portion; and a housing suction flow path formed between an outer surface of the fan housing and an inner surface of the case, the housing suction flow path allowing air which is suctioned through the suction portion to flow toward the filter member therethrough. The housing suction flow path may include a first inlet portion or inlet having a first set or predetermined width; and a second inlet portion or inlet allowing air which passes through the first inlet portion to flow therethrough, the second inlet portion having a second set or predetermined width greater than the first width.

The fan housing may include a first main body having a first set or predetermined diameter; and a third main body having a second set or predetermined diameter smaller than the first set diameter. The fan housing may further include a second main body which extends to be inclined such that a diameter of the second main body is decreased toward the third main body from the first main body.

The fan housing may be installed or provided on or at an upper side of the filter member. The air which is suctioned through the suction portion may pass through the filter member in a radial direction, and flow in an upward direction toward the fan housing.

The suction portion may include a lower suction portion or inlet formed at a height corresponding to the filter member, and an upper suction portion or inlet disposed or provided on or at an upper side of the filter member. The housing suction flow path may communicate with the upper suction portion.

The air cleaner may further include a filter frame that supports the filter member, the filter frame being coupled to the lower side of the fan housing. The filter member may have a cylindrical shape, and be slidably coupled in the radial direction toward the filter frame. The fan housing may include a first cut-out portion or cut-out which may be formed by cutting out at least a portion of the third main body, and support the filter frame.

The air cleaner may further a sensor mounting portion or mount provided in the filter frame, in which a sensor device or sensor may be installed or provided, and a second cut-out portion or cut-out provided in the fan housing, the second cut-out portion supporting the sensor mounting portion.

The filter frame may include a frame inner wall; a frame outer wall that surrounds the frame inner wall; and a housing insertion portion formed between an inner circumferential surface of the frame outer wall and an outer circumferential surface of the frame inner wall. At least a portion of the fan housing may be inserted into the housing insertion portion.

The suction portion may be formed in a circumferential direction along an outer circumferential surface of the case, to guide suction of air in 360-degree directions relative to a center line in a vertical direction that passes by an inside center of the case.

The filter frame may include a first frame forming a lower portion of the filter frame; a second frame forming an upper portion of the filter frame; and a first filter supporting portion or support that extends in the upward direction toward the second frame from the first frame. A mounting space of the filter member may be defined by the first and second frames and the first filter supporting portion.

The air cleaner may further include a locking projection that protrudes in the radial direction from the inner circumferential surface of the case, and a locking portion formed in the first frame, the locking portion being coupled to the locking projection.

The case may include a first case having a first suction portion or inlet, and a second suction portion or outlet provided on or at an upper side of the first case, the second suction portion having a second suction portion.

The fan housing may include a first fan housing installed in an inside of the first case, and a second fan housing installed or provided in an inside of the second case. The housing suction flow path may be formed in the inside of each of the first case and the second case.

The air cleaner may further include a base configured to be placed on a ground, and a suction grill coupled to an upper side of the base, the suction grill supporting a lower portion of the case.

The air cleaner may further include a suction hole provided in the suction grill, the suction hole guiding suction of air to the inside of the case, and a base suction portion or inlet formed in a space between the base and the suction grill, the base suction portion guiding air to the suction hole.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air cleaner, comprising:
   a case including a first suction inlet, the first suction inlet including a lower suction inlet and an upper suction inlet;
   a fan housing provided inside of the upper suction inlet, the fan housing accommodating a fan therein;
   a filter provided at a suction side of the fan, the filter filtering foreign materials in air which is suctioned through the first suction inlet, the filter being provided inside of the lower suction inlet and having an upper end portion located below a lower end portion of the fan housing; and
   a housing suction flow path formed between an outer surface of the fan housing and the upper suction inlet, the housing suction flow path allowing air which is suctioned through the upper suction inlet to flow toward and through the filter, wherein the housing suction flow path includes:
      a first flow path inlet having a predetermined first width; and
      a second flow path inlet through which air having passed through the first flow path inlet flows, the second flow path inlet having a second width greater than the first width, and wherein an uppermost suction portion of the upper suction inlet is located above the upper end portion of the filter such that air suctioned through the uppermost suction portion of the upper suction inlet flows downward and passes through the filter.

2. The air cleaner according to claim 1, wherein the fan housing includes:
   a first main body having a first inner width; and
   a second main body having a second inner width smaller than the first inner width.

3. The air cleaner according to claim 2, wherein the fan housing includes a third main body that extends at an incline such that an inner width of the third main body decreases toward the second main body from the first main body.

4. The air cleaner according to claim 1, wherein the housing suction flow path communicates with the upper suction inlet.

5. The air cleaner according to claim 1, wherein the fan housing is provided at an upper side of the filter, and wherein air which is suctioned through the first suction inlet passes through the filter in the radial direction, and flows in an upward direction toward the fan housing.

6. The air cleaner according to claim 5, further including a filter frame that supports the filter, the filter frame being coupled to a lower side of the fan housing.

7. The air cleaner according to claim 6, wherein the filter has a cylindrical shape, and is slidably coupled in the radial direction to the filter frame.

8. The air cleaner according to claim 6, wherein the fan housing includes a first cut-out portion that supports the filter frame.

9. The air cleaner according to claim 8, further including:
   a sensor mounting portion provided on the filter frame, and in which a sensor device is mounted; and a second cut-out portion provided in the fan housing, the second cut-out portion supporting the sensor mounting portion.

10. The air cleaner according to claim 9, wherein the filter frame includes:
a frame inner wall;
a frame outer wall that surrounds the frame inner wall; and
a housing insertion portion formed between an inner circumferential surface of the frame outer wall and an outer circumferential surface of the frame inner wall, wherein at least a portion of the fan housing is inserted into the housing insertion portion.

11. The air cleaner according to claim 1, wherein the first suction inlet is formed on an outer circumferential surface of the case, along a circumferential direction, to guide suction of air in 360-degree directions, with respect to a center line in a vertical direction that passes by an inside center of the case.

12. The air cleaner according to claim 6, wherein the filter frame includes:
a first frame that forms a lower portion of the filter frame;
a second frame that forms an upper portion of the filter frame; and
a first filter support that extends in an upward direction toward the second frame from the first frame, wherein a mounting space of the filter is defined by the first and second frames and the first filter support.

13. The air cleaner according to claim 12, further including:
a locking projection that protrudes in a radial direction from an inner circumferential surface of the case; and
a locking portion formed on the first frame, the locking portion being coupled to the locking projection.

14. The air cleaner according to claim 13, wherein the case includes:
a first case having the first suction inlet; and
a second case provided at an upper side of the first case, the second case having a second suction inlet.

15. The air cleaner according to claim 14, wherein the fan housing includes:
a first fan housing provided inside of the first case; and
a second fan housing provided inside of the second case, wherein the housing suction flow path is formed inside of each of the first case and the second case.

16. The air cleaner according to claim 1, further including:
a base configured to be located on a ground; and
a suction grill coupled to an upper side of the base, the suction grill supporting a lower portion of the case.

17. The air cleaner according to claim 16, further including:
a suction hole provided in the suction grill, the suction hole guiding suction of air to an inside of the case; and
a base suction inlet formed in a space between the base and the suction grill, the base suction inlet guiding air to the suction hole.

18. The air cleaner according to claim 1, wherein the case has a cylindrical or cone shape.

19. The air cleaner according to claim 1, wherein the lower suction inlet and the upper suction inlet are arranged in a circumferential direction of the case.

20. The air cleaner according to claim 1, wherein the first flow path inlet is located above the second flow path inlet such that air passing through first flow path flows downward and passes through the second flow path.

21. The air cleaner according to claim 20, wherein the first second flow path inlet is located above the upper end portion of the filter such that air flowing through second flow path flows downward and passes through the filter.

* * * * *